(12) United States Patent
Conlon et al.

(10) Patent No.: US 9,700,341 B2
(45) Date of Patent: Jul. 11, 2017

(54) LOADING FEATURES FOR ULTRASONIC SURGICAL INSTRUMENT

(71) Applicant: Ethicon Endo-Surgery, Inc., Cincinnati, OH (US)

(72) Inventors: Sean P. Conlon, Loveland, OH (US); David J. Cagle, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 442 days.

(21) Appl. No.: 14/140,694

(22) Filed: Dec. 26, 2013

(65) Prior Publication Data
US 2015/0182249 A1 Jul. 2, 2015

(51) Int. Cl.
A61B 17/32 (2006.01)
A61B 18/14 (2006.01)
A61B 17/00 (2006.01)

(52) U.S. Cl.
CPC ........ *A61B 17/320068* (2013.01); *A61B 17/320092* (2013.01); *A61B 18/1442* (2013.01); *A61B 2017/0046* (2013.01); *A61B 2017/00353* (2013.01); *A61B 2017/00367* (2013.01)

(58) Field of Classification Search
CPC ........ A61B 17/320068; A61B 18/1442; A61B 17/320092; A61B 2017/00353; A61B 2017/00367; A61B 2017/0046
See application file for complete search history.

(56) References Cited

U.S. PATENT DOCUMENTS

| | | | |
|---|---|---|---|
| 5,322,055 A | 6/1994 | Davisson et al. | |
| 5,873,873 A | 2/1999 | Smith et al. | |
| 5,980,510 A | 11/1999 | Tsonton et al. | |
| 6,325,811 B1 | 12/2001 | Messerly | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,752,749 B2 | 6/2014 | Moore et al. | |
| 8,986,302 B2 | 3/2015 | Aldridge et al. | |
| 2001/0031975 A1* | 10/2001 | Whitman ........... A61B 10/0233 606/167 |
| 2006/0079874 A1 | 4/2006 | Faller et al. | |

(Continued)

FOREIGN PATENT DOCUMENTS

EP 2 145 588 A1 1/2010

OTHER PUBLICATIONS

U.S. Appl. No. 13/657,553, filed Oct. 22, 2012.

(Continued)

*Primary Examiner* — Richard Louis
(74) *Attorney, Agent, or Firm* — Frost Brown Todd LLC

(57) ABSTRACT

A surgical instrument includes a body, a shaft assembly, an end effector, a transducer assembly, and a loading assembly. The end effector is coupled with a distal end of the shaft assembly. The transducer assembly is removably coupled with the proximal end of the shaft assembly. The loading assembly comprises an actuator that is operable to couple the distal end of the transducer assembly with the proximal end of the shaft assembly. The loading assembly is operable to drive the transducer assembly through at least two stages of rotation to couple the distal end of the transducer assembly with the proximal end of the shaft assembly.

20 Claims, 32 Drawing Sheets

(56) References Cited

U.S. PATENT DOCUMENTS

| | | | |
|---|---|---|---|
| 2007/0191713 A1 | 8/2007 | Eichmann et al. | |
| 2007/0282333 A1 | 12/2007 | Fortson et al. | |
| 2008/0188844 A1* | 8/2008 | McGreevy | A61B 18/082 606/28 |
| 2008/0200940 A1 | 8/2008 | Eichmann et al. | |
| 2008/0243106 A1* | 10/2008 | Coe | A61B 17/00234 606/1 |
| 2010/0069940 A1 | 3/2010 | Miller et al. | |
| 2012/0112687 A1 | 5/2012 | Houser et al. | |
| 2012/0116265 A1 | 5/2012 | Houser et al. | |
| 2013/0076271 A1* | 3/2013 | Suda | B25F 5/021 318/3 |
| 2013/0324998 A1* | 12/2013 | Kimball | A61B 17/320068 606/41 |
| 2014/0005701 A1 | 1/2014 | Olson et al. | |

OTHER PUBLICATIONS

U.S. Appl. No. 61/410,603, filed Nov. 5, 2010.
International Search Report dated Mar. 19, 2015 for Application No. PCT/US2014/072044, 4 pgs.
International Preliminary Report on Patentability and Written Opinion dated Jun. 28, 2016 for Application No. PCT/US2014/072044, 7 pgs.

\* cited by examiner

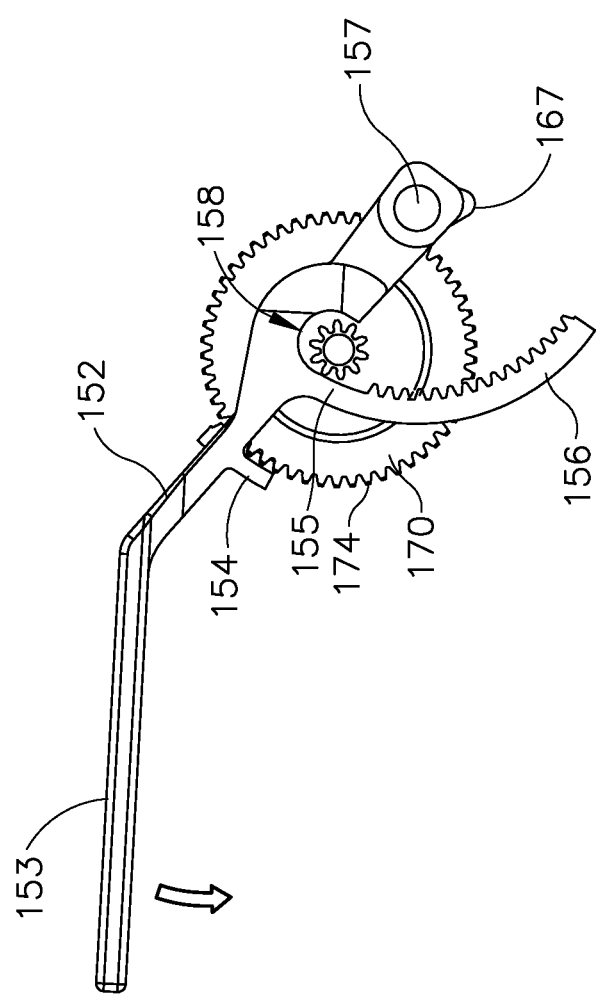

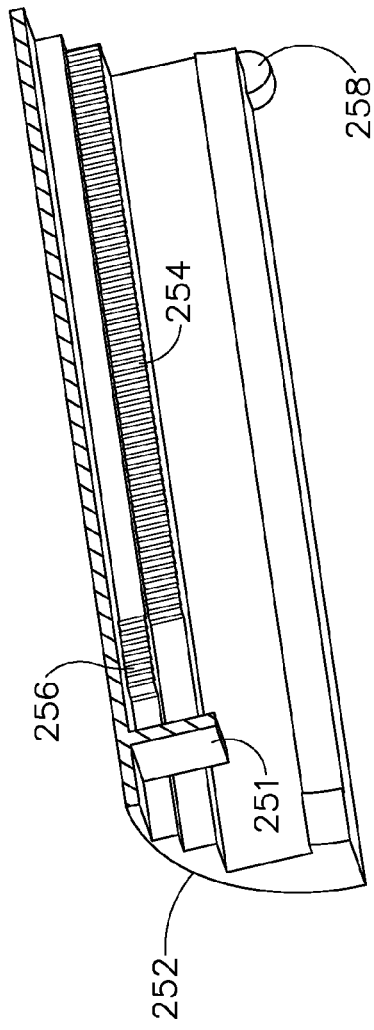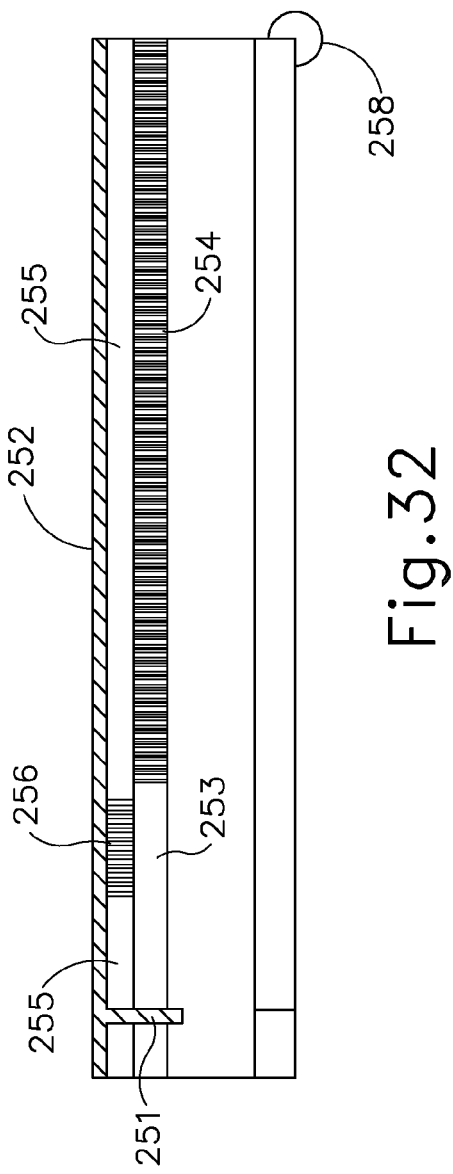

LOADING FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,623,027, issued on Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, entitled "Surgical Instruments with Articulating Shafts," now U.S. Pat. No. 9,393,037, issued on Jul. 19, 2016, the disclosure of which is incorporated by reference herein; and U.S. patent application Ser. No. 13/657,553, filed Oct. 22, 2012, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 18C depicts a cross sectional view of the loading assembly of FIG. 18A, showing the lever in a further lowered position;

FIG. 31 depicts a perspective cross-sectional view of half of the actuator of FIG. 30, taken along line 31-31 of FIG. 30;

FIG. 32 depicts a side cross-sectional view of the actuator of FIG. 30, taken along line 31-31 of FIG. 30, showing a first rack and a second rack;

Figure 1:
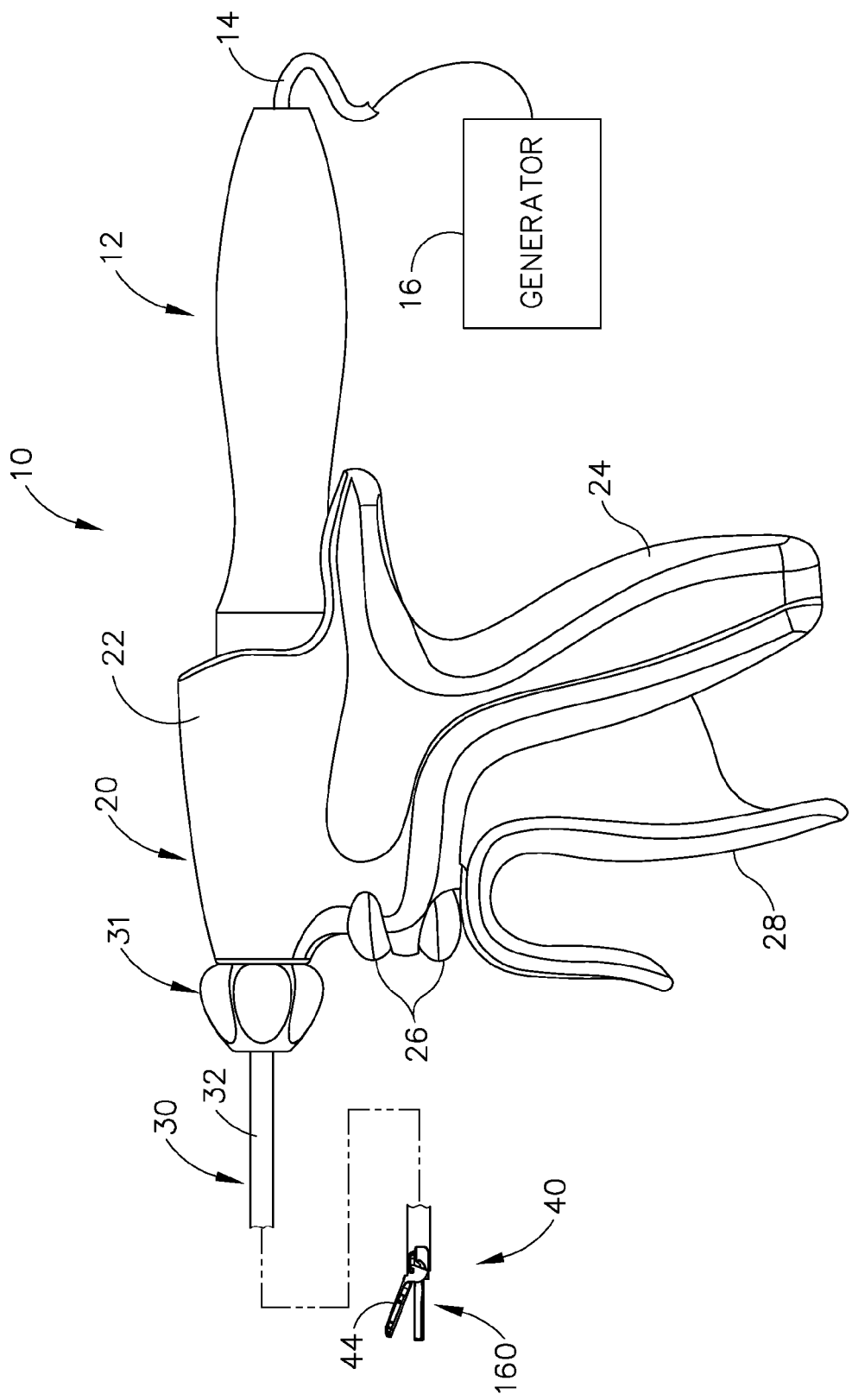
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S.

Pat. No. 6,773,444; U.S. Pat. No. 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027, issued on Jan. 7, 2014; U.S. Pub. No. 2010/0069940, now U.S. Pat. No. 9,023,071, issued on May 5, 2015; U.S. Pub. No. 2011/0015660, now U.S. Pat. No. 8,461,744, issued on Jun. 11, 2013; U.S. Pub. No. 2012/0112687, now U.S. Pat. No. 9,381,058, issued on Jul. 5, 2016; U.S. Pub. No. 2012/0116265; U.S. patent application Ser. No. 13/538,588, now U.S. Pat. No. 9,393,037, issued on Jul. 19, 2016; U.S. patent application Ser. No. 13/657,553, now U.S. Pat. No. 9,095,367, issued on Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (60) and a pivoting clamp arm (44). Clamp arm (44) is coupled with trigger (28) such that clamp arm (44) is pivotable toward ultrasonic blade (60) in response to pivoting of trigger (28) toward pistol grip (24); and such that clamp arm (44) is pivotable away from ultrasonic blade (60) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302issued on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

End effector (40) of the present example comprises clamp arm (44) and ultrasonic blade (160). Clamp arm (44) includes a clamp pad that is secured to the underside of clamp arm (44), facing blade (160). Clamp arm (44) is operable to selectively pivot toward and away from blade (160) to selectively clamp tissue between clamp arm (44) and blade (160) in response to pivoting of trigger (28) toward pistol grip (24). Blade (160) of the present example is operable to vibrate at ultrasonic frequencies in order to effectively cut through and seal tissue, particularly when the tissue is being clamped between clamp arm (44) and blade (160). Blade (160) is positioned at the distal end of an acoustic waveguide (not shown), which extends through shaft assembly (30) to form an acoustic drivetrain with transducer assembly (12) to vibrate blade (160). By way of example only, the acoustic drivetrain may be configured in accordance with various teachings of various references that are cited herein.

In the present example, the distal end of blade (160) is located at a position corresponding to an anti-node associated with resonant ultrasonic vibrations communicated through the acoustic waveguide, in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the acoustic waveguide to reach blade (160), thereby providing oscillation of blade (160) at the resonant ultrasonic frequency. Thus, when tissue is secured between blade (160) and clamp arm (44), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

II. Exemplary Ultrasonic Surgical Instrument Loading Features

In some versions, shaft assembly (30) and/or transducer assembly (12) are removable from instrument (10). By way of example only, providing removability of shaft assembly (30) from the rest of instrument (10) may facilitate a method of disposal where shaft assembly (30) is discarded after use and the rest of instrument (10) is reprocessed for re-use. In addition or in the alternative, removability of shaft assembly (30) may provide modularity where the same handle assembly (20) and transducer assembly (12) may be detachably coupled with various kinds of shaft assemblies (30), enabling an operator to easily change shaft assemblies (30) to provide different kinds of end effectors (40) (e.g., with different blade (160) configurations, etc.). Moreover, enabling separation and subsequent attachment of shaft assembly (30) relative to the rest of instrument (10) may promote reduction in package length for unused or otherwise sterile versions of instrument (10). It may therefore be desirable to provide loading features with instrument (10) to allow the user to couple shaft assembly (30) with transducer assembly (12) with relative ease. The examples below include several merely illustrative versions of such loading features that may be readily introduced into instrument (10).

A. Exemplary Lever Loading Assembly

Figure 2:
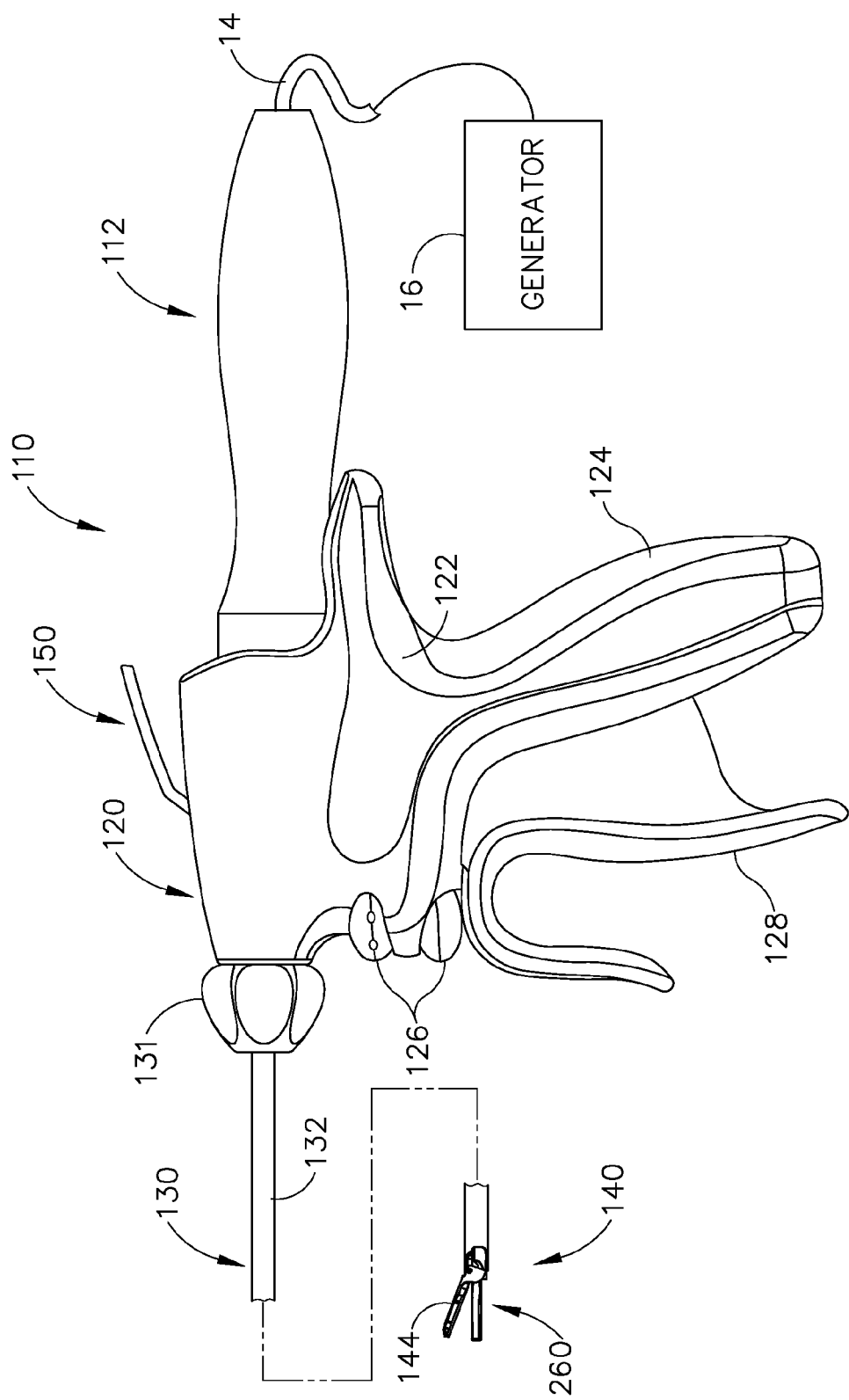
FIG. 2 depicts a side elevational view of another exemplary ultrasonic surgical instrument with a loading assembly.

FIG. 2 shows an exemplary ultrasonic surgical instrument (110) that is similar to instrument (10) in that instrument (110) comprises a handle assembly (120), a shaft assembly (130), an end effector (140), and a transducer assembly (112). Instrument (110) further comprises a loading assembly (150). End effector (140) is similar to end effector (40) In that end effector (140) comprises an ultrasonic blade (260) and a clamp arm (144). Handle assembly (120) is similar to handle assembly (20) in that handle assembly (120) comprises a body (122) including a pistol grip (124), a pair of buttons (126), and a trigger (128) that is pivotable toward and away from pistol grip (124). Trigger (128) is operable to pivot clamp arm (144) of end effector (140) toward and away from blade (260) to selectively clamp tissue between clamp arm (144) and blade (260). Blade (260) is operable to vibrate at ultrasonic frequencies in order to effectively cut through and seal tissue, particularly when the tissue is being clamped between clamp arm (144) and blade (260).

Figure 3:
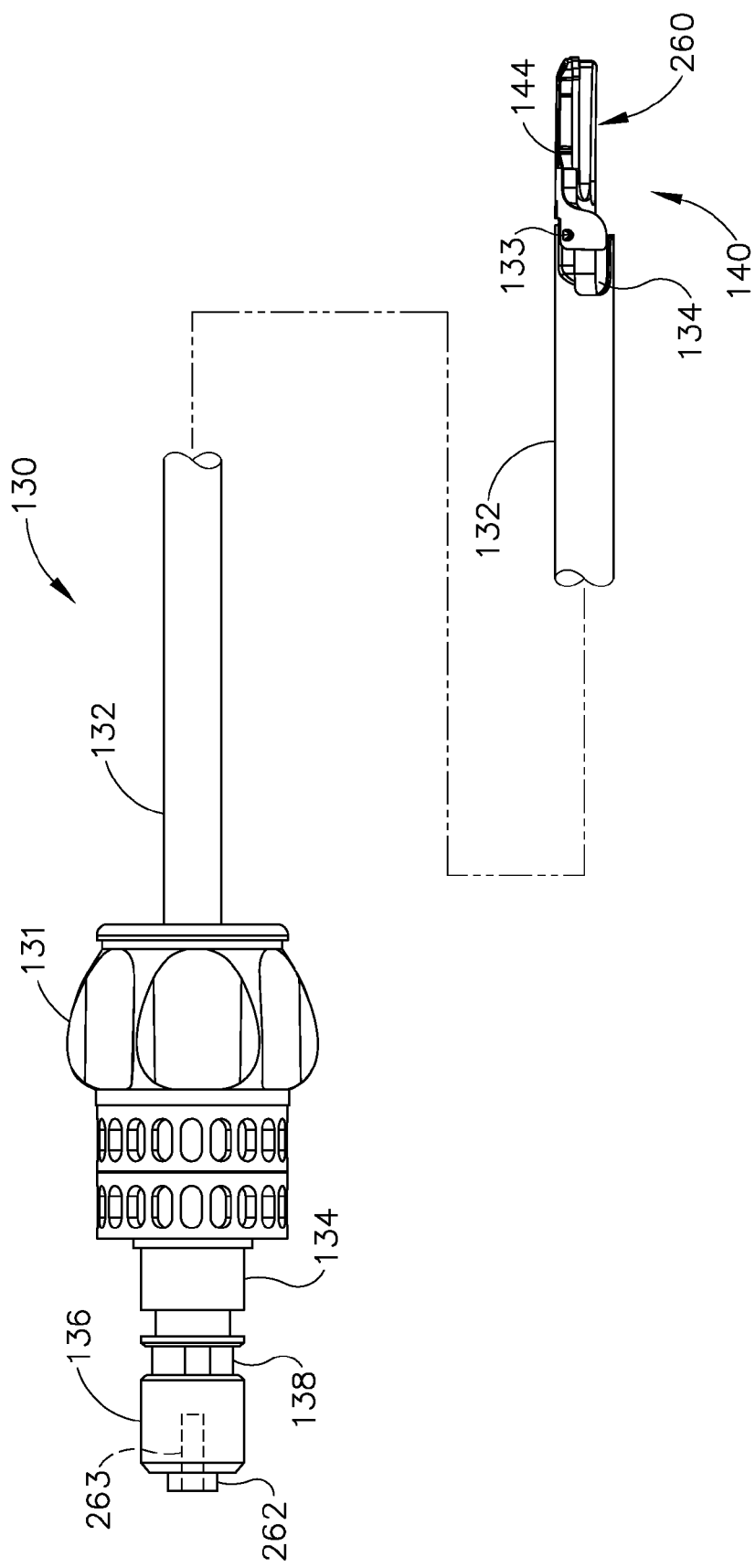
FIG. 3 depicts a side elevational view of a shaft and end effector assembly of the instrument of FIG. 2.
Figure 4A:
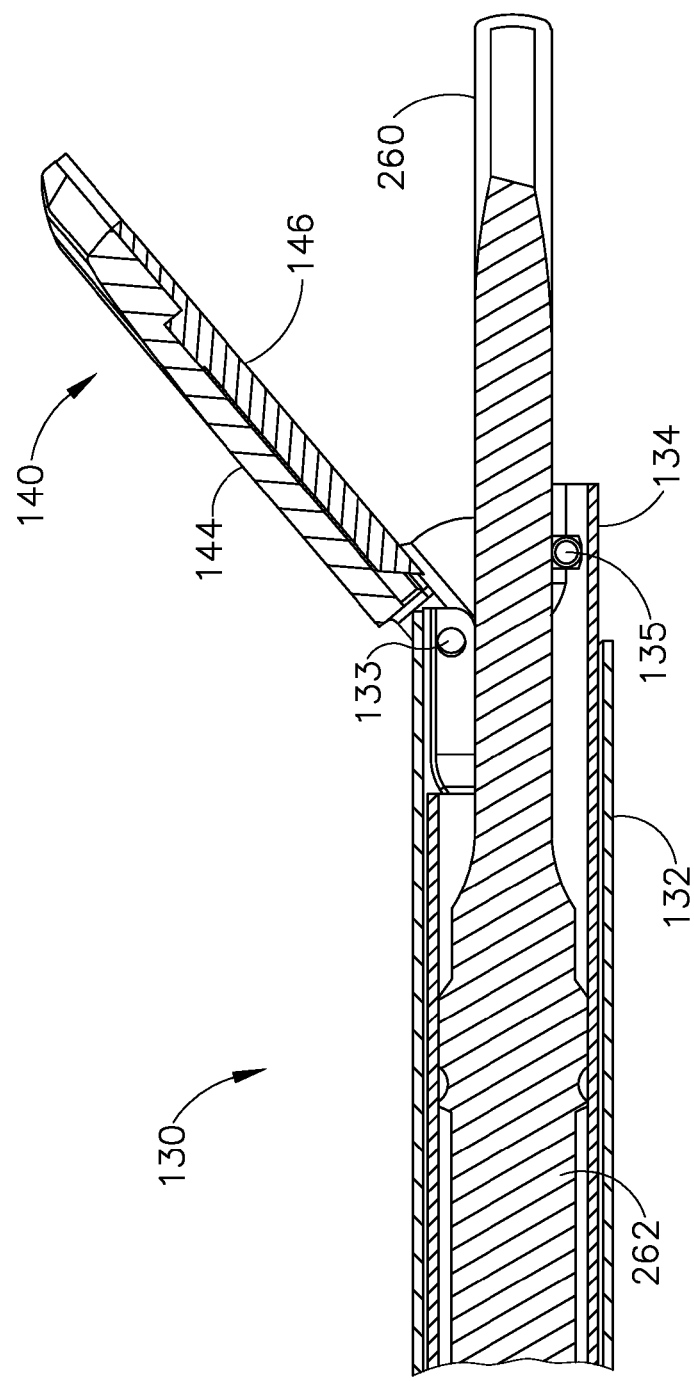
FIG. 4A depicts a cross sectional view of the end effector assembly of FIG. 3 in an open configuration.
Figure 4B:
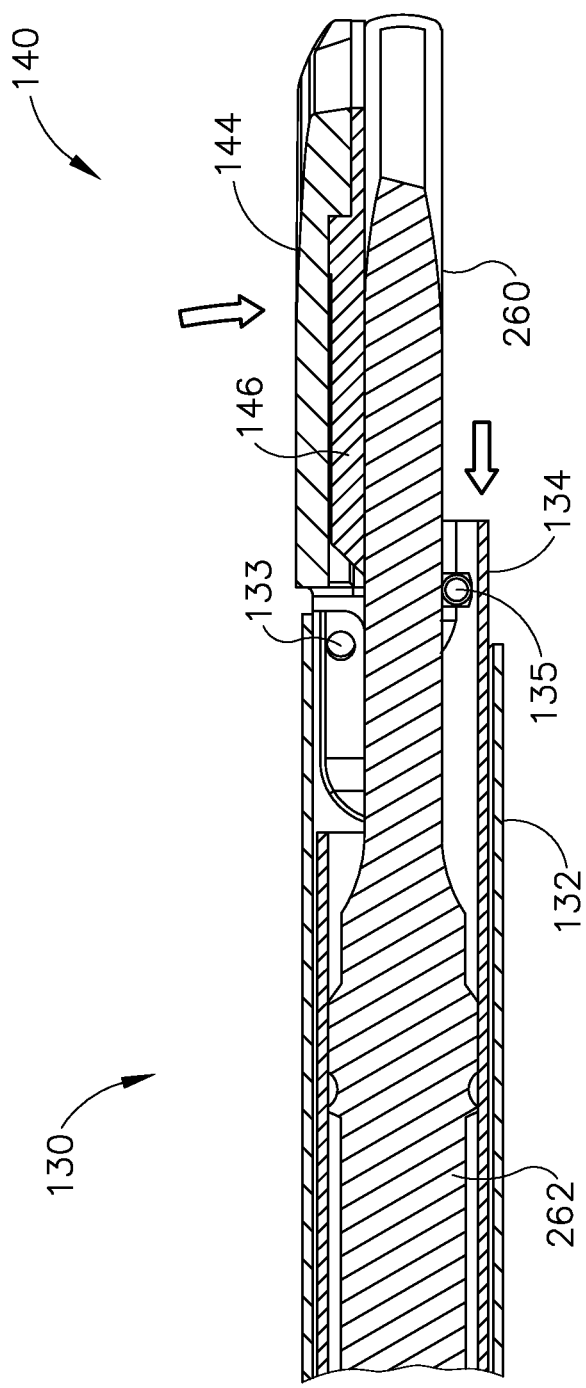
FIG. 4B depicts a cross sectional view of the end effector assembly of FIG. 3 in a closed configuration.

FIGS. 3-4B show shaft assembly (130), which comprises an outer sheath (132), an inner tube (134) slidably disposed within outer sheath (132), and a waveguide (262) disposed within inner tube (134). Inner tube (134) is coupled with trigger (128) via a coupling member (136), as will be described in more detail below. Inner tube (134) is configured to translate within outer sheath (132), in response to pivoting of trigger (128) toward and away from pistol grip (124), to selectively pivot clamp arm (144) toward and away from blade (260) of end effector (140), which is coupled to a distal end of shaft assembly (130). FIGS. 4A-4B show the longitudinal translation of inner tube (134), which causes actuation of clamp arm (144) at end effector (140). As best seen in FIG. 4A, clamp arm (144) is pivotally coupled with outer sheath (132), above ultrasonic blade (260), by a pin (133). Clamp arm (144) is also pivotally coupled with the distal end of inner tube (134), below ultrasonic blade (260), via a pin (135). Thus, longitudinal translation of inner tube (134) relative to outer sheath (132) and handle assembly (120) causes rotation of clamp arm (144) about pin (135) toward and away from ultrasonic blade (260) to thereby clamp tissue between clamp arm (144) and ultrasonic blade (262) to cut and/or seal the tissue. FIG. 4A shows clamp arm (144) in an open position relative to blade (260). FIG. 4B shows that proximal longitudinal translation of inner tube (134) relative to outer sheath (132) and handle assembly (120) causes clamp arm (144) to move toward ultrasonic blade (260). Distal longitudinal translation of inner tube (134) relative to outer sheath (132) and handle assembly (120) causes clamp arm (144) to move away from ultrasonic blade (260) to return clamp arm (144) to the position shown in FIG. 4A. Clamp arm (144) includes a clamp pad (146) mounted on clamp arm (144) for cooperation with blade (260). For example, pivotal movement of the clamp arm (144) positions clamp pad (144) in a substantially parallel relationship to, and in contact with, blade (260) (and/or tissue adjacent to blade) to thereby define a tissue treatment region, as shown in FIG. 4B. By this construction, tissue is clamped between clamp pad (146) and blade (260).

Shaft assembly (130) is similar to shaft assembly (30), with the proximal end of an acoustic waveguide (262) being selectively removable from transducer assembly (112). Waveguide (262) extends through shaft assembly (130) and is in acoustic communication with blade (260), such that waveguide (262) is configured to communicate ultrasonic vibrations from transducer assembly (112) to blade (260) when waveguide (262) is coupled with transducer assembly (112). As shown in FIG. 3, the proximal end of waveguide (262) extends proximally from the proximal end of inner tube (134). The proximal end of waveguide (262) includes a threaded recess (263) that may be coupled with a threaded stud (67) of transducer assembly (112), which is similar to transducer assembly (12). When threaded stud (67) is fully seated in threaded recess (263), transducer assembly (112) and waveguide (262) are mechanically and acoustically coupled together to form an acoustic assembly.

Figure 5:
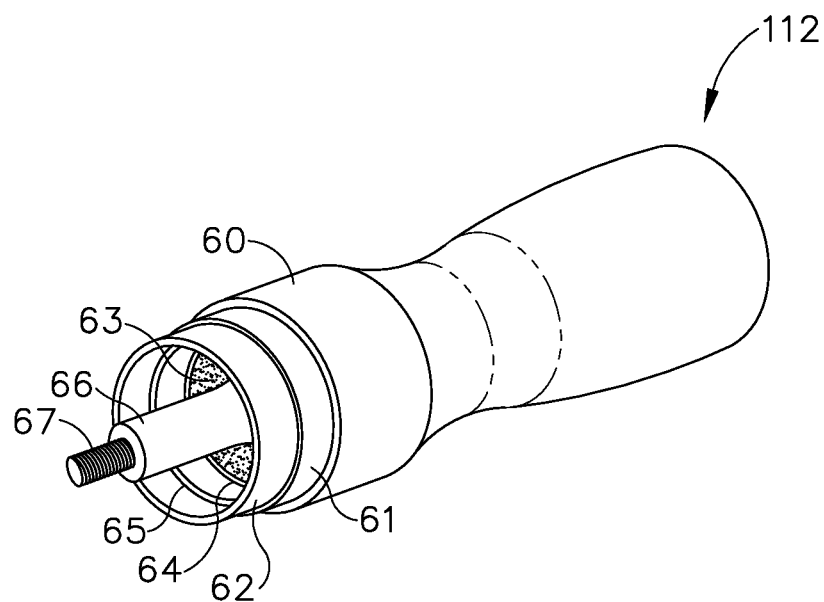
FIG. 5 depicts a perspective view of a transducer assembly of the instrument of FIG. 2.

As shown in FIG. 5, transducer assembly (112) of the present example includes a housing (60), which is acoustically isolated from ultrasonically vibrating elements of transducer assembly (112). The distal end of transducer assembly (112) includes a first conductive ring (65) and a second conductive ring (64), which are both disposed within housing (60) of transducer assembly (112). First conductive ring (65) comprises a ring member that is disposed between housing (60) and a horn (66), which extends distally from housing (60). Horn (66) comprises a threaded stud (67) extending distally therefrom such that horn (66) may be threadably coupled with threaded recess (263) formed in the proximal end of waveguide (262). First conductive ring (65) is formed adjacent to, or as part of a flange (61) within a transducer cavity (62) such that first conductive ring (65) is electrically isolated from second conductive ring (64) and other conductive components of transducer assembly (112). First conductive ring (65) is located on a non-conductive platform extending distally from housing (60). First conductive ring (65) is electrically coupled to a cable, such as cable (14) shown in FIG. 2, by one or more electrical wires or conductive etchings (not shown) within housing (60).

Second conductive ring (64) of transducer assembly (112) similarly comprises a ring member that is disposed between housing (60) and horn (66). Second conductive ring (64) is disposed between first conductive ring (65) and horn (66). As is shown in FIG. 5, first and second conductive rings (64, 65) are concentric members that are longitudinally offset from each other, with conductive ring (64) also being positioned at a greater radial distance from the central axis shared by conductive rings (64, 65). Second conductive ring (64) is likewise electrically isolated from first conductive ring (65) and other conductive components of transducer assembly (112). Similar to first conductive ring (65), second conductive ring (64) extends from the non-conductive platform. One or more washer-shaped spacers (63) may be disposed between first and second conductive rings (64, 65) or between the rings (64, 65) and other members of transducer assembly (112). Second conductive ring (64) is also electrically coupled to a cable, such as cable (14) shown in FIG. 2, by one or more electrical wires or conductive etchings (not shown) within housing (60). One merely exemplary suitable ultrasonic transducer assembly (112) is Model No. HP054, sold by Ethicon Endo-Surgery, Inc. of Cincinnati, Ohio.

As previously discussed, threaded stud (67) at the distal end of transducer assembly (112) threadably couples with threaded recess (263) formed in the proximal end of waveguide (262). The distal end of transducer assembly (112) also interfaces with one or more electrical connections (not shown) via first and second conductive rings (64, 65) to electrically couple transducer assembly (112) to buttons (126) to provide a user with finger-activated controls for activating transducer assembly (112) while using surgical instrument (110). In some variations, first and second conductive rings (64, 65) may be omitted from the distal end of transducer assembly (112) and the electrical coupling of transducer assembly (112) to buttons (126) may be accomplished by alternative structures, such as conductors at the proximal end of transducer assembly (112), conductors located along the side of housing (60) of transducer assembly (112), directly from cable (14), and/or any other structures and configurations as will be apparent to one of ordinary skill in the art in view of the teachings herein.

Figure 6:
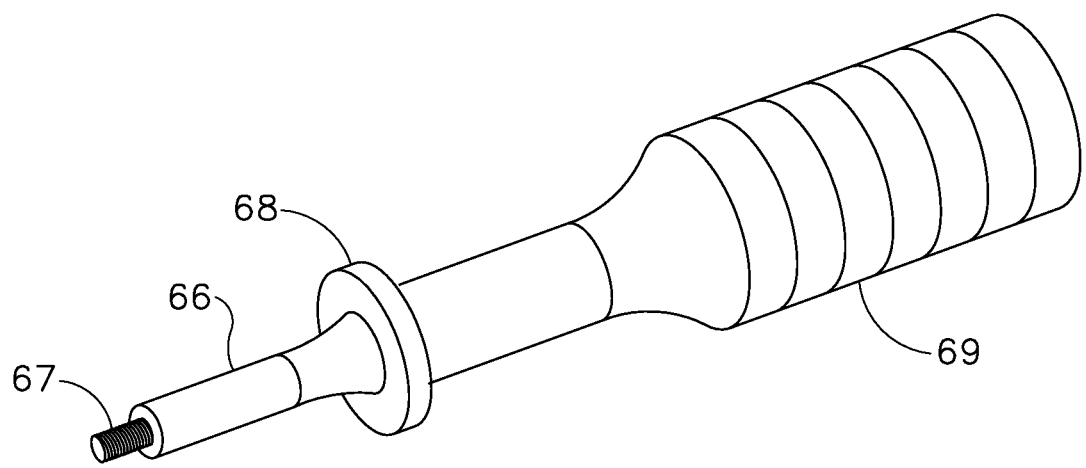
FIG. 6 depicts a perspective view of the transducer assembly of FIG. 5 with a housing removed.

FIG. 6 depicts transducer assembly (112) with housing (60) removed. Mounting flange (68) near the distal end of transducer assembly (112) and piezoelectric stack (69) at the proximal end of transducer assembly (112) can be viewed with housing (60) removed. When transducer assembly (112) of the present example is activated via a button (126), an electric field is created in piezoelectric stack (69), causing piezoelectric stack (69) and horn (66) to oscillate within and relative to housing (60). Mounting flange (68) is used to couple horn (66) to housing (60), to thereby support piezoelectric stack (69) in housing (60). Mounting flange (68) is located at a node associated with resonant ultrasonic vibrations communicated from piezoelectric stack (69) to horn (66). Transducer assembly (112) is operable to create mechanical energy, or vibrations, at an ultrasonic frequency (such as 55.5 kHz). If transducer assembly (112) is coupled to waveguide (262) via horn (66), then these mechanical oscillations are transmitted through waveguide (262) to ultimately reach blade (260). Thus, when tissue is clamped between ultrasonic blade (260) and clamp arm (144), the ultrasonic oscillation of ultrasonic blade (260), as generated by transducer assembly (112) and communicated to blade (260) via horn (66) and waveguide (262), may sever and/or seal the tissue. While some features and configurations for transducer assembly (112) have been described, still other suitable features and configurations for transducer assembly (112) will be apparent to one of ordinary skill in the art in view of the teachings herein.

Figure 7:
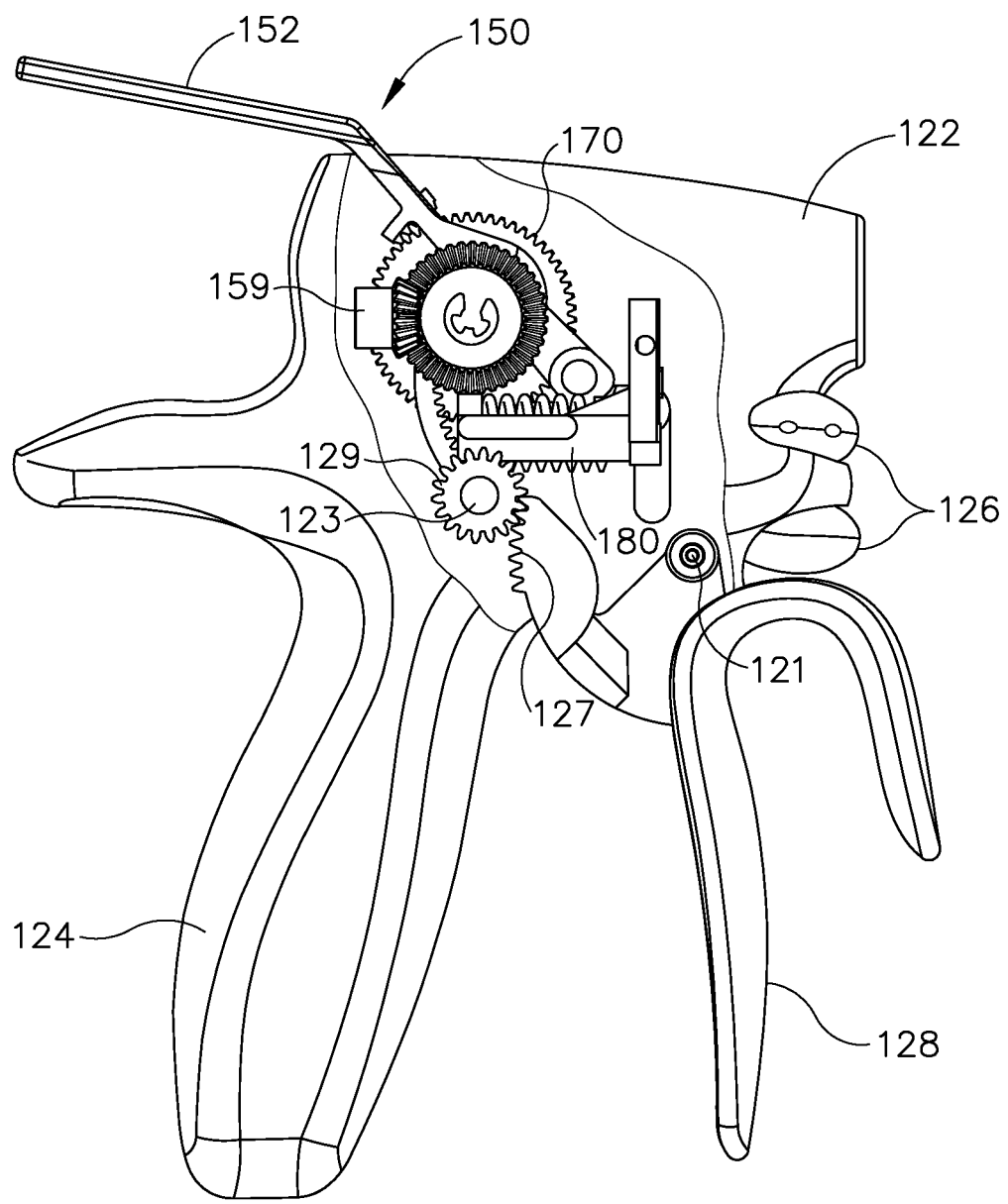
FIG. 7 depicts a cross sectional view of a handpiece assembly of the instrument of FIG. 2, showing the loading assembly.
Figure 8:
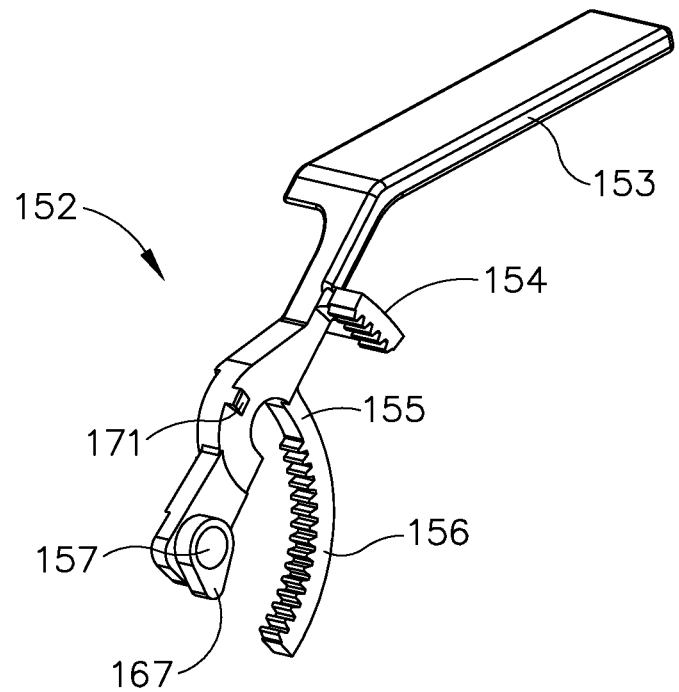
FIG. 8 depicts a perspective view of a lever of the loading assembly of FIG. 7.
Figure 9:
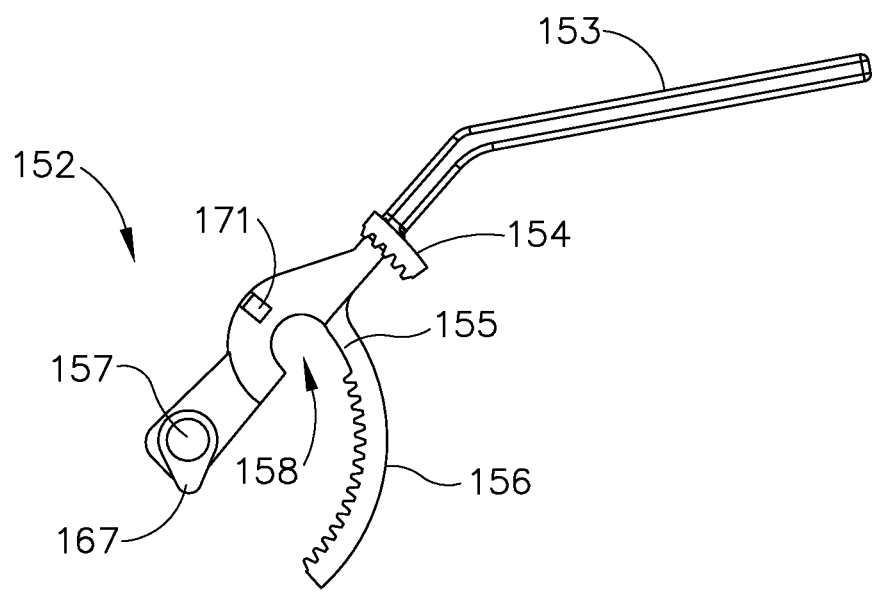
FIG. 9 depicts a side elevational view of the lever of FIG. 8.

FIG. 7 shows an exemplary loading assembly (150) that may be used to couple transducer assembly (112) with shaft assembly (130). Loading assembly (150) is housed within body (122) of handle assembly (120) and includes a lever (152), a coupling gear (170), a bevel gear (159), and a shaft support assembly (180). As best seen in FIGS. 8-9, lever (152) comprises a first rack (156), a second rack (154), an extension (153), a post hole (157), a teardrop cam (167), and a lateral cam feature (171). Post hole (157) is coupled with body (122) via a pin (not shown) such that lever (152) is pivotable relative to body (122) about post hole (157). First rack (156) includes a section having a plurality of teeth and a smooth portion (155). First rack (156) is curved along an arc defined by a first radius of curvature extending from the axis defined by post hole (157).

Second rack (154) also includes a plurality of teeth. As best seen in FIG. 8, second rack (154) is laterally offset from first rack (156). Racks (154, 156) thus extend along different, parallel planes that are perpendicular to the pivot axis defined by post hole (157). Second rack (154) is curved along an arc defined by a second radius of curvature extending from the axis defined by post hole (157). The second radius of curvature is greater than the first radius of curvature. Second rack (154) is positioned to correspond with smooth portion (155) of first rack (156). In particular, as best seen in FIG. 9, second rack (154) extends along substantially the same angular range from the pivot axis defined by post hole (157) as the angular range along which smooth portion (155) extends. Extension (153) extends outwardly such that extension (153) protrudes proximally from body (122) to allow a user to grasp or otherwise engage extension (153) to pivot lever (152) about the axis defined by post hole (157). Teardrop cam (167) has a teardrop shape and is configured to selectively couple shaft support assembly (180) with shaft assembly (130) as will be discussed in further detail below. Lever (152) is positioned to engage coupling gear (170).

Figure 10:
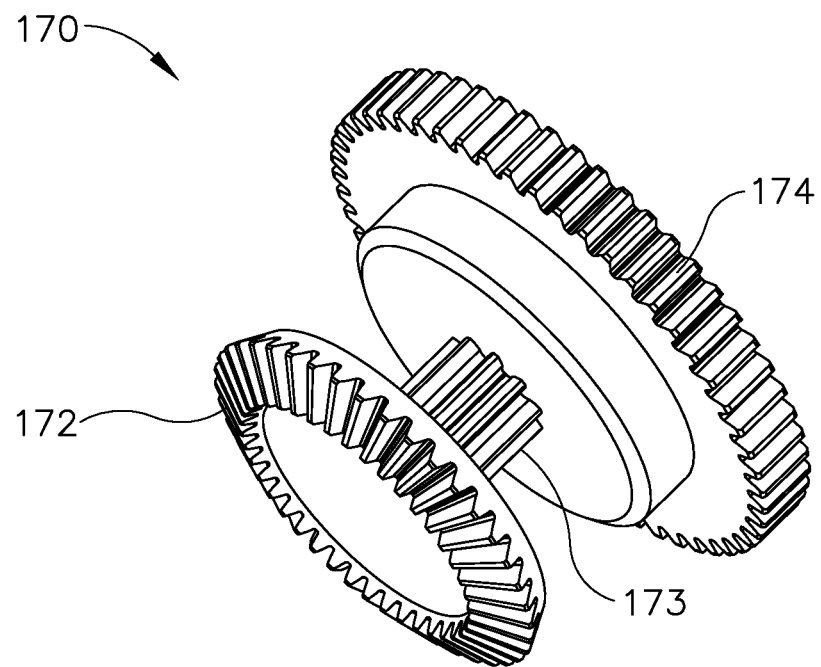
FIG. 10 depicts a perspective view of a coupling gear of the loading assembly of FIG. 7.

As shown in FIG. 10, coupling gear (170) comprises a first spur gear (173) and a second spur gear (174) that is laterally offset from first spur gear (173). Coupling gear (170) is configured to rotate within body (122) about a rotation axis extending through the center of coupling gear (170). Coupling gear (170) is also configured to translate within body (122) along the same rotation axis. Second spur gear (174) has a greater diameter than first spur gear (173). First spur gear (173) is configured to engage first rack (156) of lever (152) and second spur gear (174) is configured to engage second rack (154) of lever (152). Accordingly, when lever (152) is pivoted relative to body (122), first rack (156) engages first spur gear (173) to rotate coupling gear (170) at a relatively high speed and relatively low torque. After lever (152) completes a first range of pivotal motion and continues to pivot further, first spur gear (173) enters smooth portion (155) of first rack (156) to disengage the teeth of first rack (156). Second rack (154) then engages second spur gear (174) to rotate coupling gear (170) at a lower speed and a higher torque than first spur gear (173) as lever (152) travels through a second range of pivotal motion.

Figure 11:
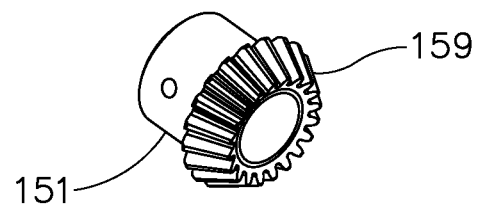
FIG. 11 depicts a perspective view of a bevel gear of the loading assembly of FIG. 7.
Figure 12:
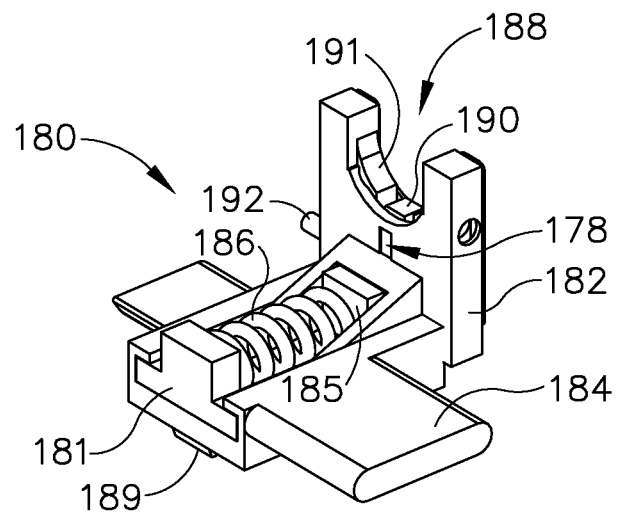
FIG. 12 depicts a top perspective view of a shaft support assembly of the loading assembly of FIG. 7.

Coupling gear (170) further comprises a bevel gear (172) that is configured to engage another bevel gear (159), which is oriented perpendicular to coupling gear (170). Accordingly, coupling gear (170) rotates to thereby rotate bevel gear (159). As best seen in FIG. 11, bevel gear (159) includes a shaft (151) extending proximally from bevel gear (159). Shaft (151) is coaxially positioned around horn (66) of transducer assembly (112) and is secured to horn (66) such that bevel gear (159) is configured to rotate horn (66) of transducer assembly (112). Accordingly, bevel gear (159) rotates horn (66) to drive threaded stud (67) of horn (66) into recess (263) of waveguide (262) to couple transducer assembly (112) with blade (260). In the present example, bevel gear (159) is acoustically isolated from transducer assembly (112). By way of example only, bevel gear (159) may be located at a longitudinal position along horn (66) corresponding to a node associated with resonant ultrasonic vibrations communicated through horn (66).

As noted above, coupling gear (170) is configured to translate within body (122) along the rotation axis of coupling gear (170). This enables bevel gear (172) to selectively engage bevel gear (159). In the present example, a coil spring, leaf spring, and/or other resilient member provides a resilient bias to coupling gear (170), thereby biasing bevel gear (172) into engagement with bevel gear (159). However, as will be described in greater detail below, lateral cam feature (171) of lever (152) is operable to engage coupling gear (170) and thereby drive coupling gear (170) along the rotation axis of coupling gear (170), to thereby disengage bevel gear (172) from bevel gear (159). This occurs when lever (152) has been pivoted to a closed position. It should be understood that disengagement of bevel gear (172) from bevel gear (159) will allow transducer assembly (112) and shaft assembly (130) to rotate freely relative to handle assembly (120).

Figure 13:
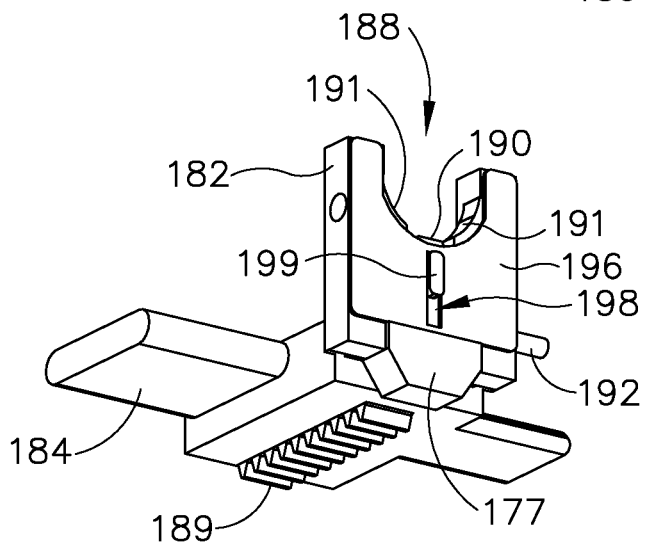
FIG. 13 depicts a bottom perspective view of the shaft support assembly of FIG. 12.
Figure 14:
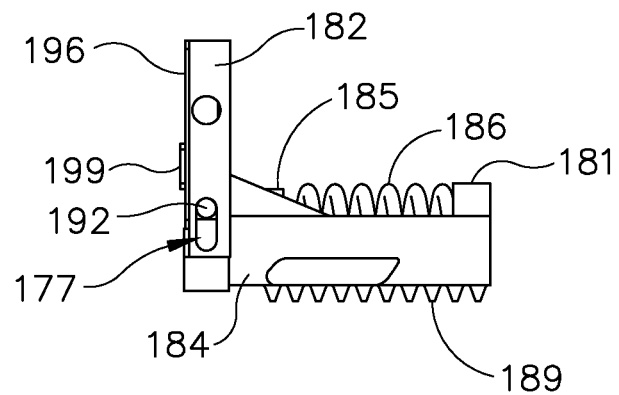
FIG. 14 depicts a side elevational view of the shaft support assembly of FIG. 12.
Figure 15:
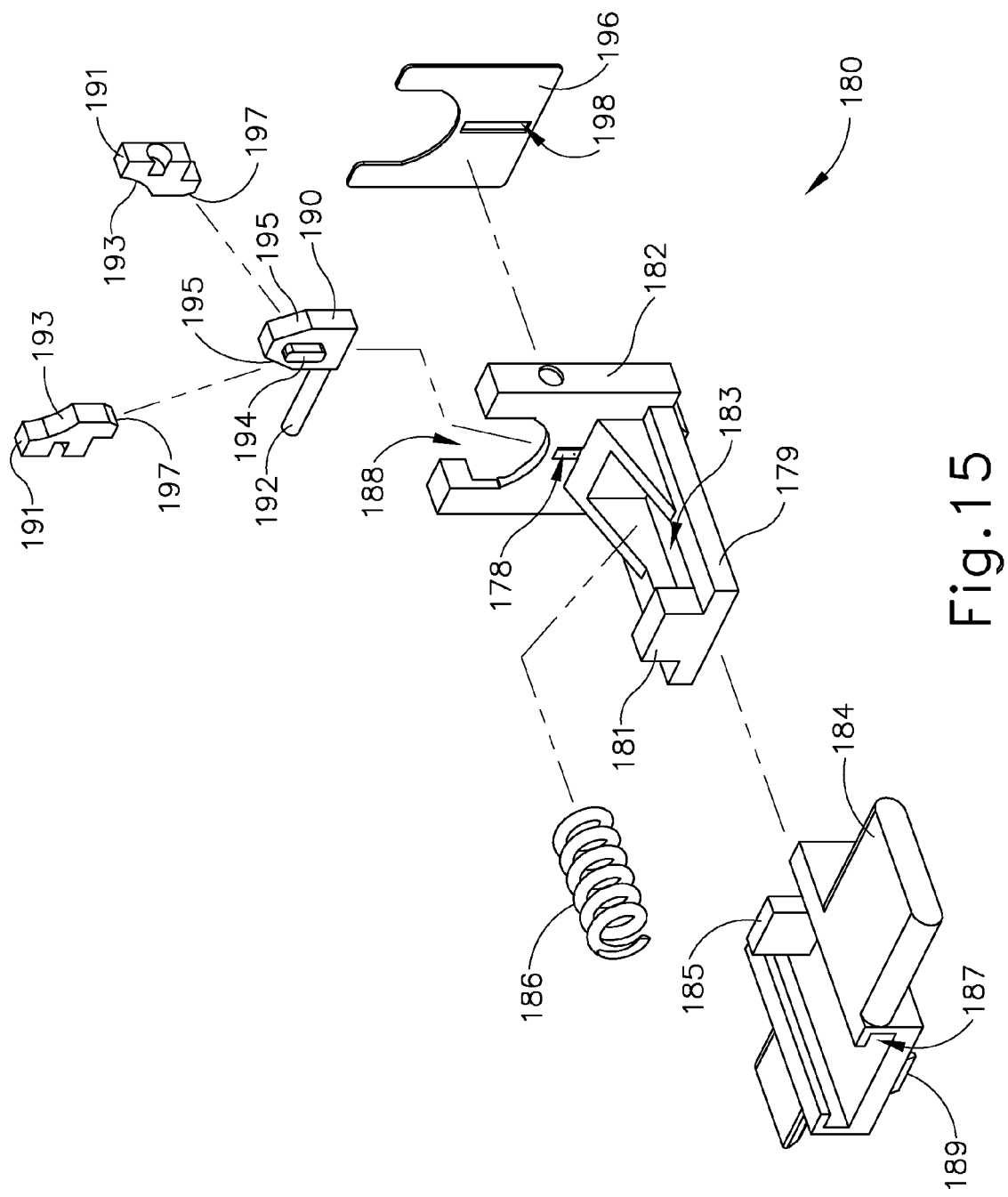
FIG. 15 depicts an exploded view of the shaft support assembly of FIG. 12.

FIGS. 12-15 show shaft support assembly (180) in greater detail. Shaft support assembly (180) is used to engage and support shaft assembly (130) adjacent to transducer assembly (112). Shaft support assembly (180) comprises a housing (184), a shaft support (182) that is translatable within housing (184), and a resilient member (186) positioned between housing (184) and shaft support (182). As best seen in FIG. 15, housing (184) defines a T-shaped channel (187), with a fixed tab (185) protruding upwardly from housing (184) in channel (187). As best seen in FIG. 13, housing (184) further includes a rack (189) downwardly from the opposing side of channel (187). Referring back to FIG. 7, rack (189) is configured to engage a spur gear (129) that is coupled with an integral rack (127) of trigger (128). Accordingly, when trigger (128) is pivoted toward and/or away from pistol grip (124), rack (127) of trigger (128) pivots to rotate spur gear (129) about pin (123). Spur gear (129) thereby translates rack (189) of housing (184) to translate shaft support assembly (180). As will be discussed in more detail below, shaft support assembly (180) engages coupling member (136) on inner tube (134) to translate inner tube (134) of shaft assembly (130), which pivots clamp arm (144) toward and/or away from blade (260) as described above with reference to FIGS. 4A-4B.

As shown in FIG. 15, shaft support (182) defines a yoke opening (188) and a tab opening (183); and further includes rails (179) and a tab (181). Yoke opening (188) is configured to receive coupling member (136) on the proximal end of inner tube (134). Tab opening (183) is configured to receive tab (185) of housing (184). Rails (179) extend along each side of shaft support (182) and are configured to be slidably inserted within T-shaped channel (187) of housing (184) to allow shaft support (182) to translate within housing (184). Tab (181) extends outwardly from shaft support (182) and is positioned proximal to yoke opening (188). Tab opening (183) is positioned between tab (181) and yoke opening (188) and is configured to receive resilient member (186). In particular, resilient member (186) is interposed between tab (181) of shaft support (182) and tab (185) of housing (184) to bias shaft support (182) distally relative to housing (184). Shaft support (182) translates proximally within housing (184) as transducer assembly (112) is threaded into shaft assembly (130) and compresses resilient member (186) to prevent transducer assembly (112) from being over-rotated into shaft assembly (130). Of course, other suitable configurations will be apparent to one with ordinary skill in the art in view of the teachings herein.

Figure 16:
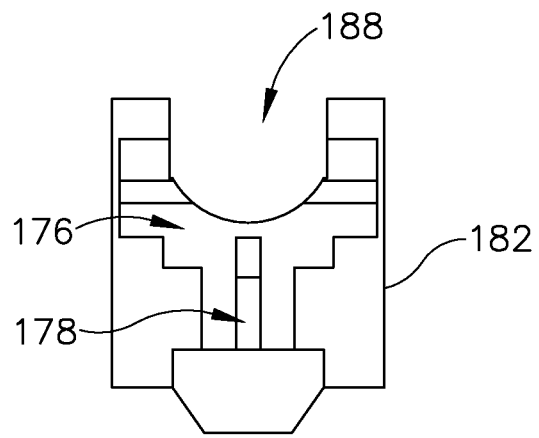
FIG. 16 depicts a front view of a shaft support of the shaft support assembly of FIG. 12.

As shown in FIG. 16, the distal face of shaft support (182) further comprises a distally facing recess (176) and a slot (178). Recess (176) is shaped to receive a retainer cam (190) and retainer members (191) shown in FIG. 15. Retainer cam (190) and retainer members (191) are positioned within recess (176) of shaft support (182) and held in lateral alignment by cover (196) secured to the distal end of shaft support (182). Retainer cam (190) includes a rod (192) extending laterally from retainer cam (190). As shown in FIG. 14, rod (192) is disposed in an elongate slot (177) that is formed through a sidewall of shaft support (182). Rod (192) is configured to translate vertically within slot (177) as retainer cam (190) translates vertically in shaft support (182). As best seen in FIGS. 13 and 15, retainer cam (190) further includes protrusions (194, 199) extending outwardly on opposing sides of retainer cam (190). Protrusion (194) extends proximally from retainer cam (190) and is configured to slide within a slot (178) of shaft support (180). Protrusion (199) extends distally and is configured to slide within an opening (198) of cover (196). Accordingly, retainer cam (190) is translatable within shaft support (182) to engage and disengage coupling member (136) of inner tube (134), as will be described in greater detail below with reference to FIGS. 21A-21B.

Figure 21A:
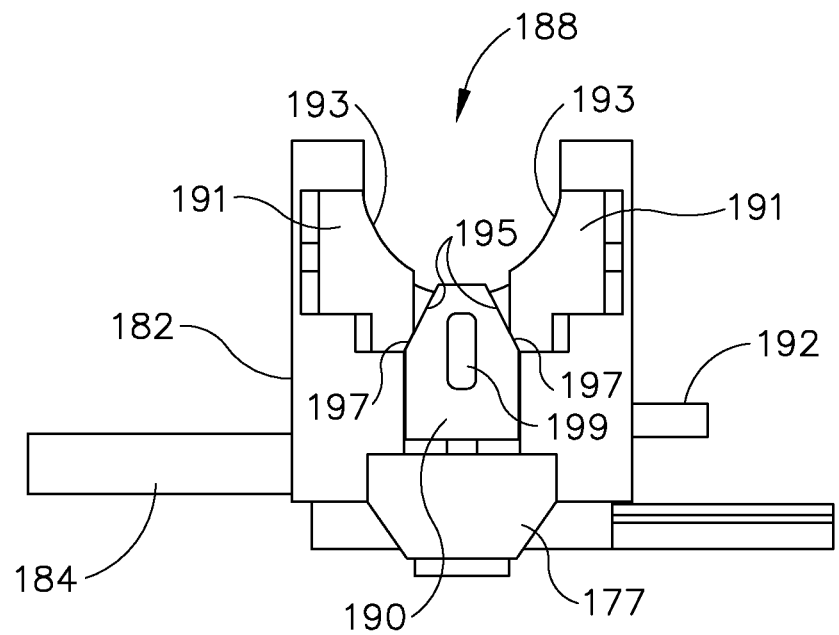
FIG. 21A depicts a front view of the shaft support assembly of FIG. 12 with a retainer cam in a raised position and retainer members in outward positions.
Figure 21B:
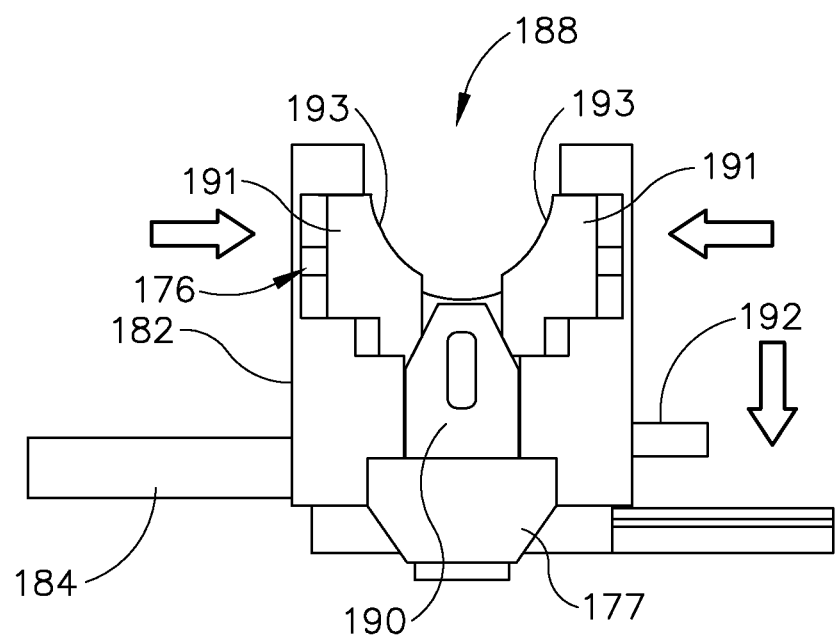
FIG. 21B depicts a front view of the shaft support assembly of FIG. 12 with the retainer cam in a lowered position and the retainer members in inward positions.

As best seen in FIG. 15 and FIGS. 21A-21B, retainer cam (190) further comprises ramped surfaces (195) that engage corresponding ramped surfaces (197) of retainer members (191). Retainer members (191) also include curved surfaces (193) that are configured to selectively engage coupling member (136) of inner tube (134) to retain inner tube (134) relative to shaft support assembly (180). Retainer members (191) are positioned within recess (176) of shaft support (182) such that curved surfaces (193) are aligned with yoke opening (188) of shaft support (182) and ramped surfaces (197) engage ramped surfaces (195) of retainer cam (190). Retainer members (191) are resiliently biased to translate inwardly into yoke opening (188) based on the vertical position of retainer cam (190) in shaft support (182). In particular, when retainer cam (190) is in a lower position in shaft support (182) as shown in FIG. 21B, retainer members (191) are located in inward positions, extended within yoke opening (188). When retainer cam (190) is in an upper position in shaft support (182) as shown in FIG. 21A, retainer members (191) are located in outward positions, retracted within shaft support (182). This lateral translation of retainer members (191) based the vertical position of retainer cam (190) is provided through a cam action imposed by ramped surfaces (195) against ramped surfaces (197). It should be understood that coil springs, leaf springs, and/or various other kinds of resilient features may be used to bias retainer members (191) toward the inward position shown in FIG. 21B. As will be described in greater detail below, when retainer members (191) are in the inward position as shown in FIG. 21B, retainer members are disposed in an annular recess (138) of coupling member (136). This engagement allows shaft assembly (130) to rotate within shaft support (182) yet prevents shaft assembly (130) from translating relative to shaft support (182).

Figure 17A:
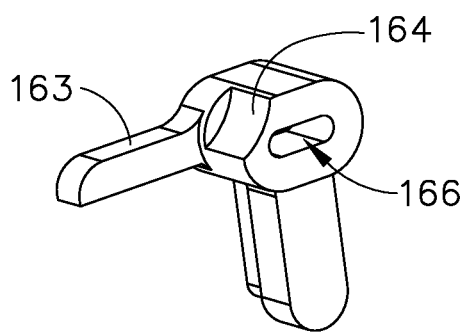
FIG. 17A depicts a perspective view of a slider of the loading assembly of FIG. 7.
Figure 17B:
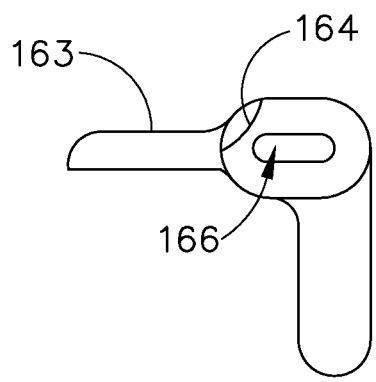
FIG. 17B depicts a side elevational view of the slider of FIG. 17A.
Figure 20A:
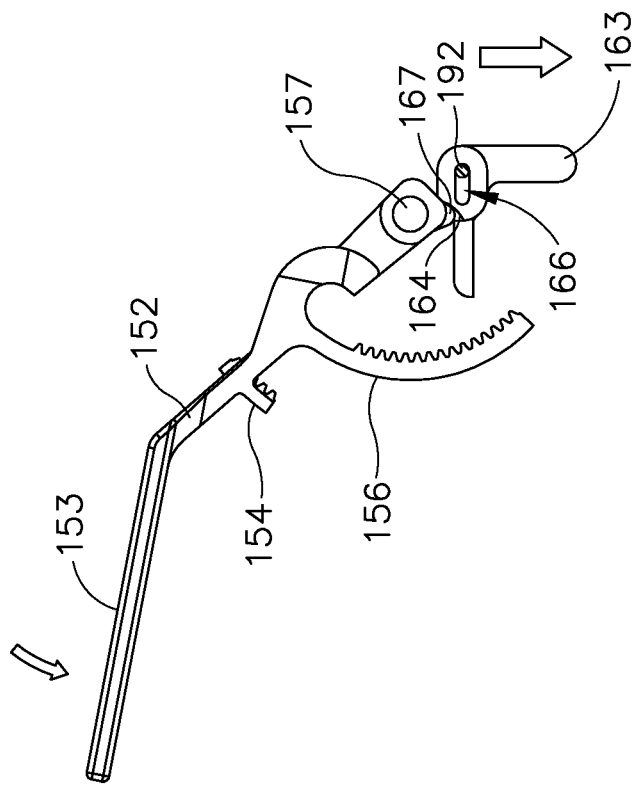
FIG. 20A depicts a side elevational view of the lever and the slider of the loading assembly of FIG. 7 with the lever and the slider in raised positions.
Figure 20B:
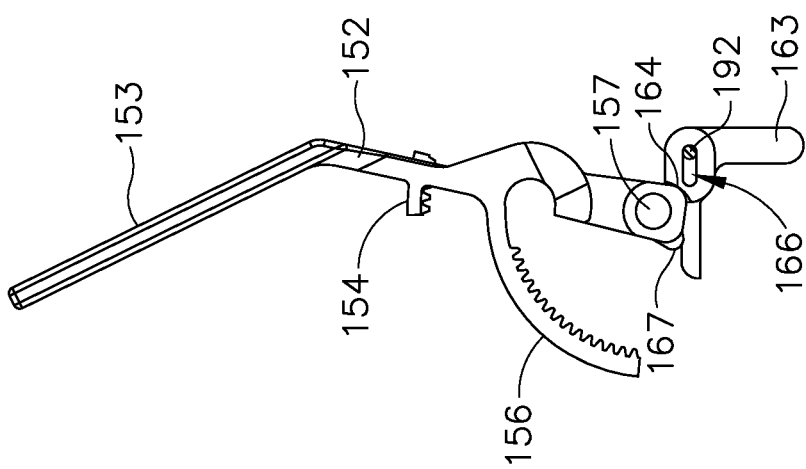
FIG. 20B depicts a side elevational view of the lever and the slider of FIG. 20A with the lever and the slider in lowered positions.

Rod (192) of retainer cam (190) is inserted within a slot (166) of a slider (163), which is shown in FIGS. 17A-17B. FIGS. 20A-20B also show rod (192) disposed in slot (166), with rod (192) being shown in cross-section. Slider (163) is slidably retained within body (122) of handle assembly (120), such that slider (163) translates vertically within body (122) without otherwise moving in relation to body (122). Slot (166) extends longitudinally along an interior surface of slider (163) to allow rod (192) to translate within slot (166).

Slider (163) further comprises a notch (164) to receive the distal end of lever (152). This allows the distal end of lever (152) to rotate within notch (164). Lever (152) is pivoted until teardrop cam (167) of lever (152) slider (163) to drive slider (163) downwardly. Slider (163) thereby drives rod (192) and retainer cam (190) downwardly, allowing retainer members (191) inwardly into engagement with annular recess (138) of coupling member (136) as will be described in greater detail below. The elongate configuration of slot (166) provides clearance for rod (192) to translate proximally along slot (166), thereby accommodating proximal longitudinal translation of shaft support assembly (180) and inner tube (134) as trigger (128) is pivoted toward pistol grip (124) to actuate clamp arm (144).

Figure 18A:
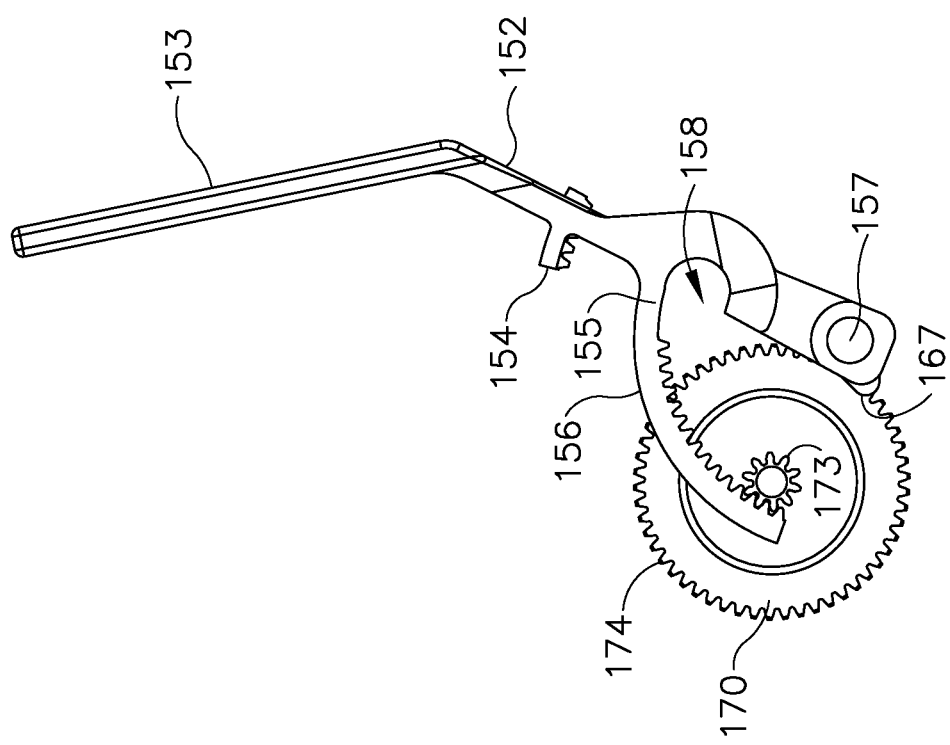
FIG. 18A depicts a cross sectional view of the loading assembly of FIG. 7, showing the lever in a raised position.

FIGS. 18A-21B show an exemplary operation of loading assembly (150). As shown in FIG. 19A, the proximal end of waveguide (262) is positioned adjacent to the distal end of horn (66) to longitudinally align threaded recess (263) of waveguide (262) with threaded stud (67) of horn (66). Shaft support (182) is at a distal position relative to housing (184) of shaft support assembly (180). As best seen in FIG. 18A, lever (152) of loading assembly (150) is in a raised position at this stage such that first rack (156) is engaged with first spur gear (173) and second rack (154) is disengaged from second spur gear (174). With lever (152) pivoted away from body (122), the distal end of lever (152) rests within notch (164) of slider (163), as shown in FIG. 20A. Rod (192) of retainer cam (190) is at an upper position within slot (166) of slider (163), as shown in FIG. 21A. With retainer cam (190) in the upper position, retainer members (191) are retracted within shaft support (182) to provide clearance for coupling member (136) of inner tube (134) in yoke opening (188) of shaft support. The proximal portion of coupling member (136) is thus positioned within yoke opening (188) of shaft support (182). It should be understood that the operator may grasp shaft assembly (130) by knob (131) to position shaft assembly (130) in relation to loading assembly (150) to the position shown in FIG. 19A.

Figure 18B:
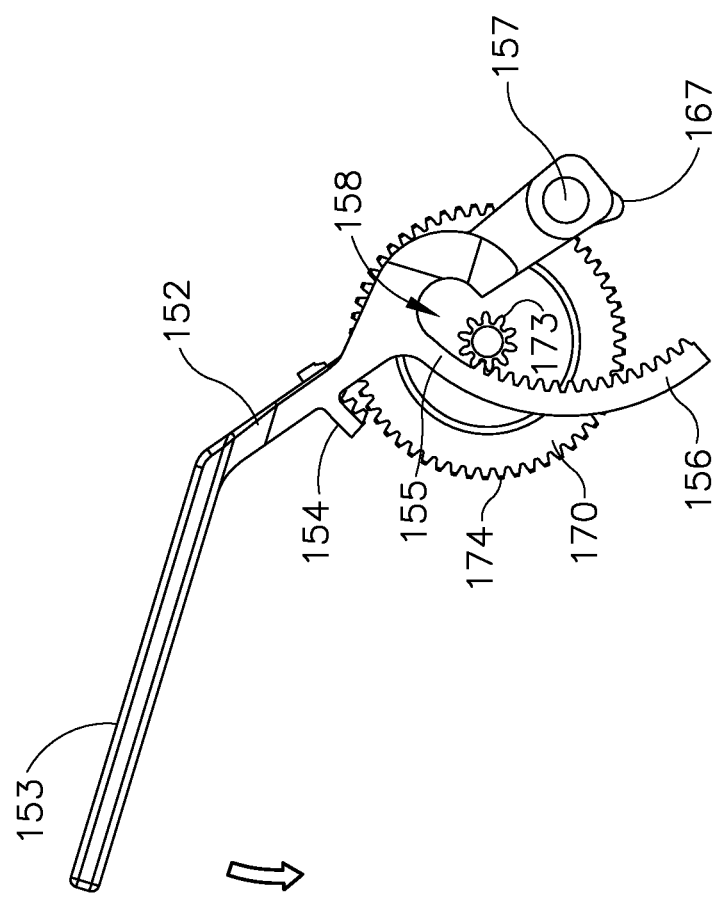
FIG. 18B depicts a cross sectional view of the loading assembly of FIG. 18A, showing the lever in a partially lowered position.

Extension (153) of lever (152) may then be grasped by a user to pivot lever (152) toward body (122) of handle assembly (120). The operator may maintain a grip on shaft assembly (130) (e.g., by grasping knob (131), etc.) to maintain the rotational position of shaft assembly (130) relative to body (122) as lever (152) is pivoted relative to body (122). As shown in FIG. 18B, the teeth of first rack (156) engage first spur gear (173) of coupling gear (170) to rotate first spur gear (173) as lever (152) is pivoted toward body (122). As shown in FIG. 19B, first spur gear (173) thereby rotates bevel gear (172) of coupling gear (170), which rotates the other bevel gear (159) coupled with horn (66) of transducer assembly (112). Threaded stud (67) of horn (66) accordingly rotates into threaded recess (263) of waveguide (262). The diameter of first spur gear (173) is sized to rotate horn (66) at a relatively high speed. For instance, first rack (156) of loading assembly (150) may cause horn (66) to rotate three complete revolutions as lever (152) is pivoted from the position shown in FIGS. 18A and 19A to the position shown in FIGS. 18B and 19B. Other suitable rotation configurations for horn (66) will be apparent to one with ordinary skill in the art in view of the teachings herein. As horn (66) is threaded into waveguide (262), the threaded engagement pulls shaft assembly (130) proximally relative to shaft support assembly (180), such that shaft support (182) reaches annular recess (138) of coupling member (136) as shown in FIG. 19B.

In the present example, when lever (152) has reached the position shown in FIGS. 18B and 19B, and when shaft support assembly (180) has reached the position shown in FIG. 19B, teardrop cam (167) has driven slider (163) downwardly from the position shown in FIG. 20A to the position shown in FIG. 20B. This downward movement of slider (163) pulls cam (190) downwardly via rod (192), from the position shown in FIG. 21A to the position shown in FIG. 21B. With cam (190) in the downward position, the resilient bias of retainer members (191) drives retainer members (191) inwardly into yoke opening (188) as shown in FIG. 21B. The inwardly positioned retainer members (191) are thus disposed in annular recess (138) of coupling member (136). The positioning of retainer members (191) in annular recess (138) prevents coupling member (136) and inner tube (134) from translating relative to shaft support (182). However, retainer members (191) still permit coupling member (136) and inner tube (134) to rotate relative to shaft support (182). It should therefore be understood that the operator may continue to maintain a grip on shaft assembly (130) (e.g., by grasping knob (131), etc.) to continue maintaining the rotational position of shaft assembly (130) relative to body (122) as lever (152) is pivoted further relative to body (122).

As the operator continues to pivot extension (153) toward body (122) while maintaining the rotational position of shaft assembly (130) relative to body (122), first spur gear (173) disengages the teeth of first rack (156) and enters smooth portion (155) of first rack (156), as shown in FIG. 18C. Second rack (154) then engages second spur gear (174). Second spur gear (174) thereby rotates bevel gear (172) of coupling gear (170), which rotates the other bevel gear (159) on horn (66), as shown in FIG. 19C. This rotates horn (66) at a lower speed and a higher torque than first spur gear (173). For instance, loading assembly (150) may generate 6 in-lbs of torque between transducer assembly (112) and shaft assembly (130) and rotate horn (66) about an additional 15 degrees to achieve a sufficient amount of torque. Of course, any other suitable amount of torque may be generated. Second rack (154) thereby sufficiently couples horn (66) with waveguide (262) at a desired torque value. During this process of completing the threading of stud (67) in recess (263) waveguide (262), shaft assembly (130) translates further proximally. This translates shaft support (182) proximally within housing (184) of shaft support assembly (180), as shown in FIG. 19C. As shaft support (182) translates proximally within housing (184), resilient member (186) compresses. In some versions, compression of resilient member (186) prevents horn (66) from being over-rotated into shaft assembly (130). It should also be understood that rod (192) translates proximally within slot (166) of slider (163) as shaft support (182) translates proximally within housing (184).

Figure 19A:
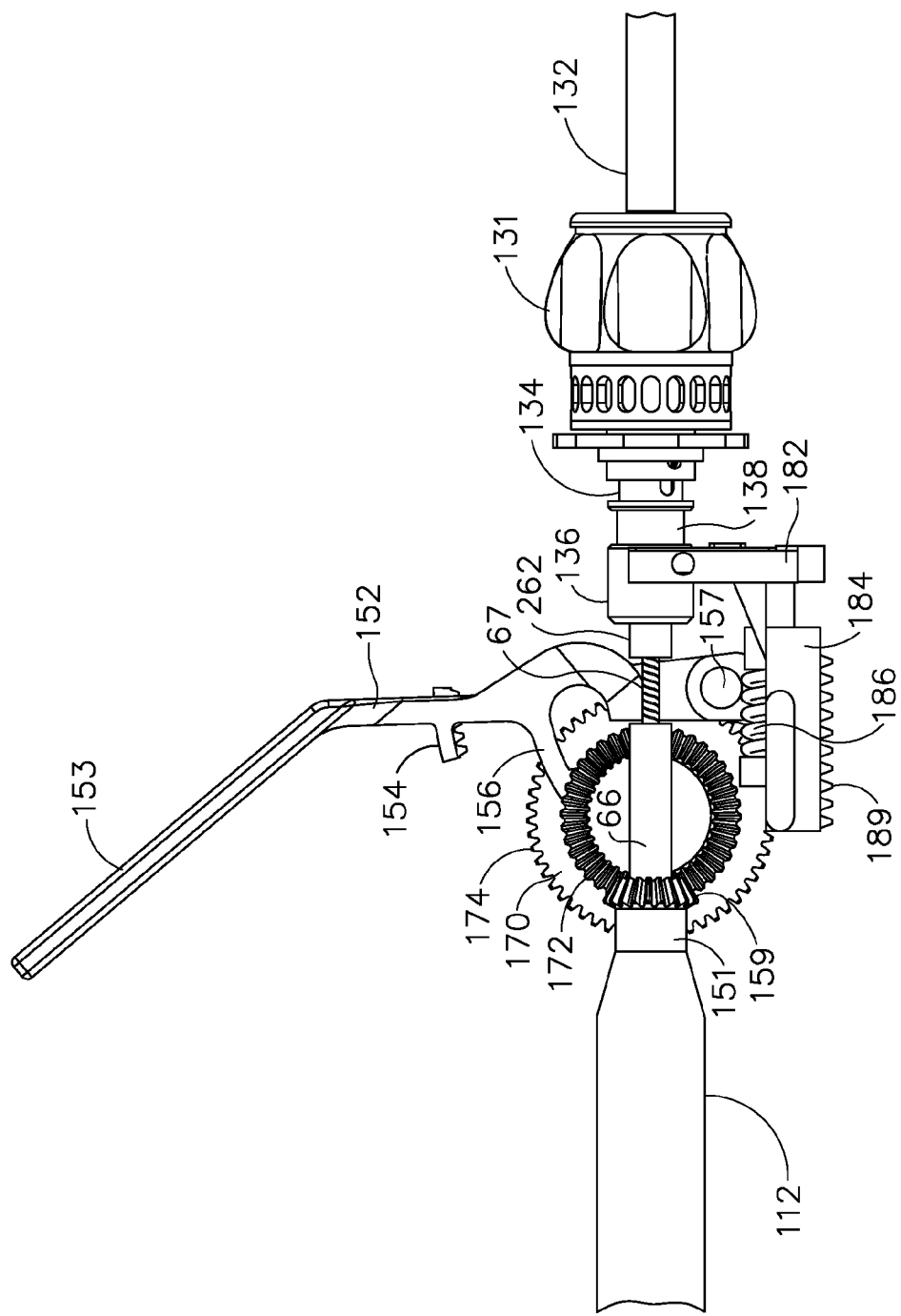
FIG. 19A depicts a cross sectional view of the instrument of FIG. 2 with the shaft assembly detached from the transducer assembly.
Figure 19B:
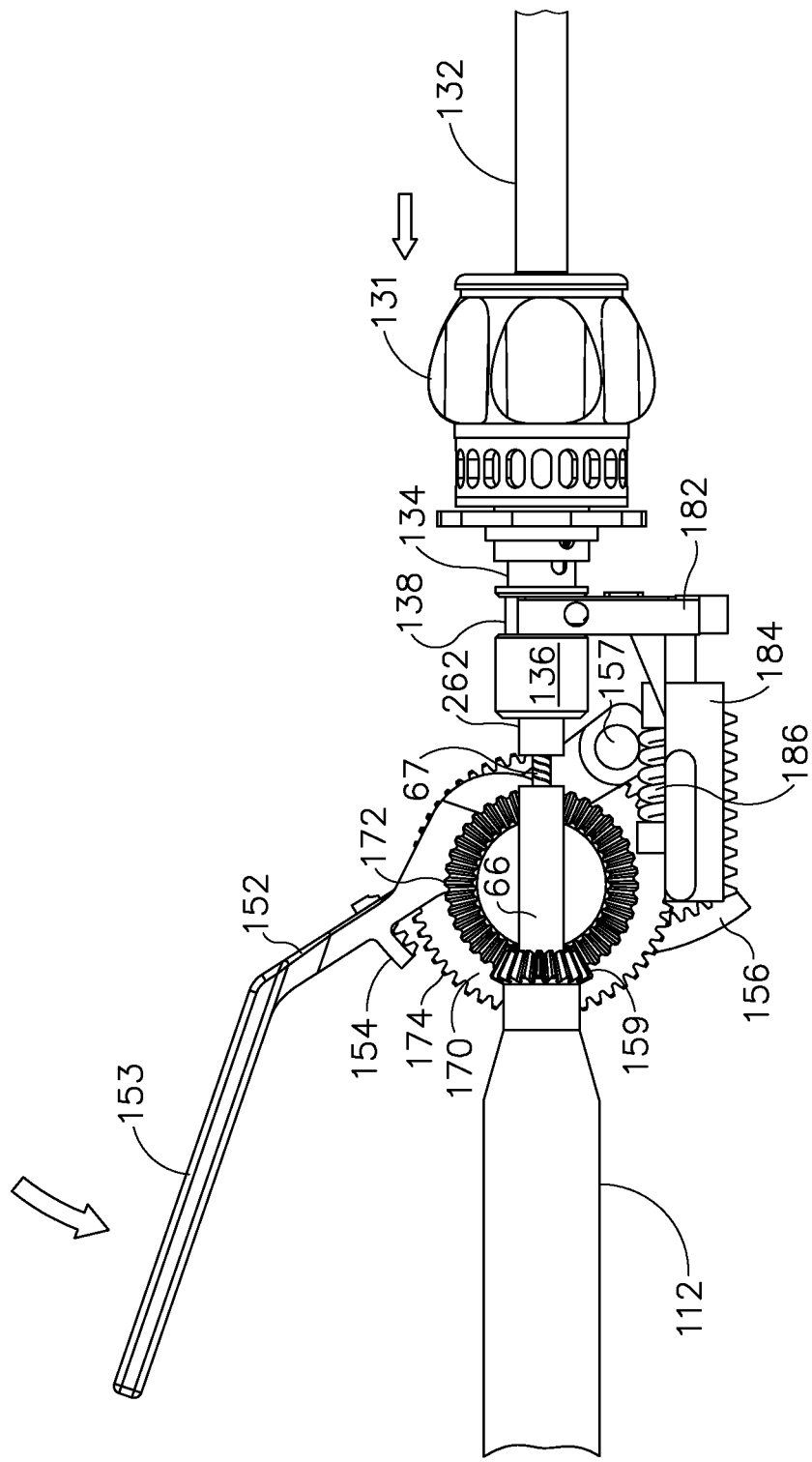
FIG. 19B depicts a cross sectional view of the instrument of FIG. 2 with the shaft assembly partially coupled with the transducer assembly.
Figure 19C:
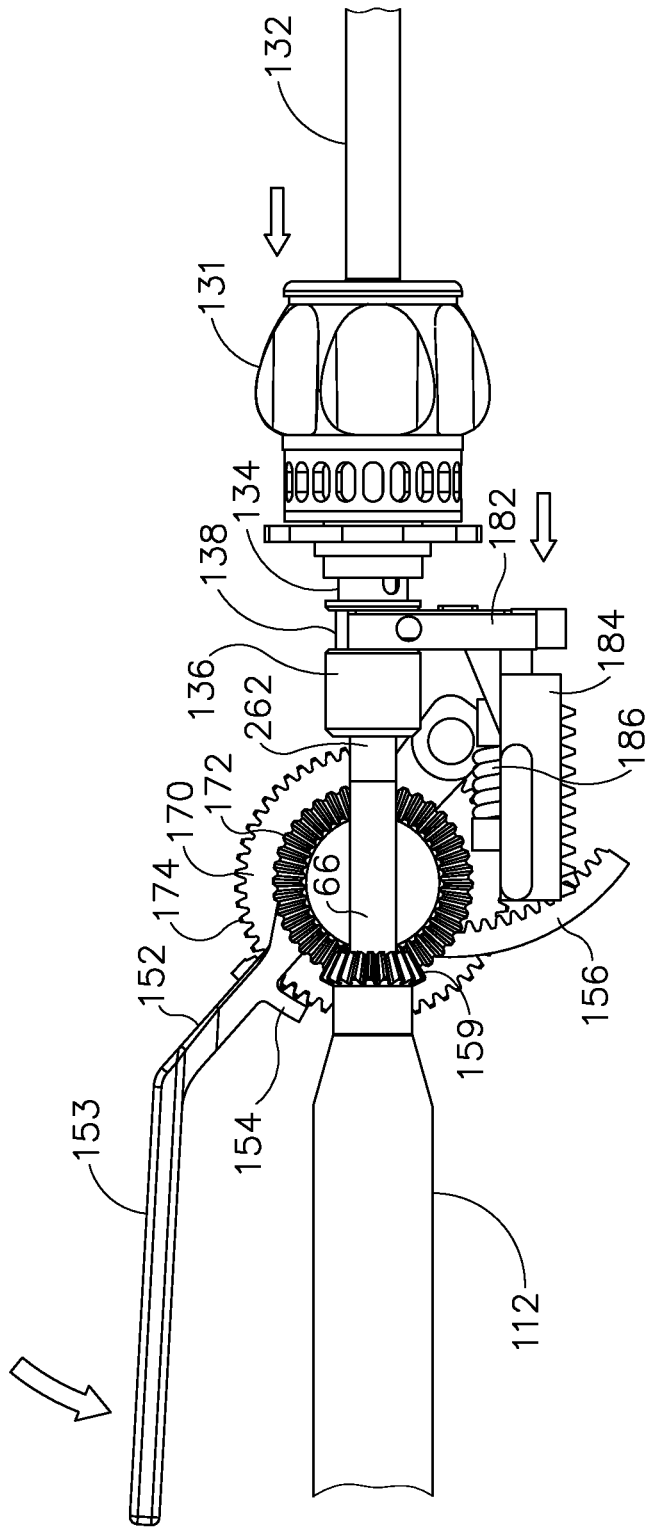
FIG. 19C depicts a cross sectional view of the instrument of FIG. 2 with the shaft assembly fully coupled with the transducer assembly.

It should be understood from the foregoing that once lever (152) has completed its pivot stroke from the position shown in FIGS. 18A and 19A to the position shown in FIGS. 18C and 19C, loading assembly (150) has fully coupled shaft assembly (150) with transducer assembly (112) and shaft support assembly (180). Thereafter, when transducer assembly (112) is activated to generate ultrasonic vibrations, those vibrations will be communicated from horn (66) to waveguide (262) and ultimately to blade (260). When trigger (128) is pivoted proximally toward pistol grip (124), shaft support assembly (180) will communicate proximal motion to inner tube (134), thereby pivoting clamp arm (144) toward blade (260). For instance, referring back to FIG. 7, trigger (128) may be pivoted relative to pistol grip (124) to translate rack (127) of trigger (128) against spur gear (129). Spur gear (129) may then rotate to translate rack (189) of housing (184). Housing (184) thereby translates shaft support (182), which is engaged with annular channel (138) of coupling member (136). This translates coupling member (136) and inner tube (134) to pivot clamp arm (144).

It should also be understood that once lever (152) has completed its pivot stroke from the position shown in FIGS. 18A and 19A to the position shown in FIGS. 18C and 19C, lateral cam feature (171) of lever (152) has driven coupling gear (170) along the rotation axis of coupling gear (170), thereby disengaging bevel gear (172) from bevel gear (159). This allows transducer assembly (112) and shaft assembly (130) to rotate freely relative to handle assembly (120). The operator may manipulate knob (131) to rotate shaft assembly (130) and transducer assembly (112) relative to handle assembly (120). With end effector (140) at the desired angular orientation, clamp arm (144) may be actuated to clamp tissue between clamp arm (144) and blade (260). Buttons (126) may then be pressed to activate transducer assembly (112) and thereby activate blade (260) to vibrate at ultrasonic frequencies in order to effectively cut through and seal tissue.

After the tissue is cut and/or sealed, shaft assembly (130) may be detached from transducer assembly (112). While the operator maintains a grip on shaft assembly (130) (e.g., by grasping knob (131), etc.) to maintain the rotational position of shaft assembly (130) relative to body (122), lever (152) of loading assembly (150) may be pivoted away from body (122) such that second rack (154) rotates second spur gear (174), bevel gear (172), and bevel gear (159) in the opposing direction to unthread transducer assembly (112) from shaft assembly (130). As lever (152) is raised, second rack (154) disengages second spur gear (174) and first rack (156) engages first spur gear (173) to continue rotating bevel gears (172, 159). Accordingly, threaded stud (67) of transducer assembly (112) is rotated to decouple horn (66) from blade (260) to release shaft assembly (130) from transducer assembly (112). Shaft assembly (130) and/or transducer assembly (112) may then be removed from instrument (110). Other suitable loading assembly (150) configurations will be apparent to one with ordinary skill in the art. For example, bevel gear (159) may be positioned around the proximal end of shaft assembly (130) such that shaft assembly (130) is rotated onto a stationary transducer assembly (112).

B. Exemplary Translational Loading Assembly

Figure 22:
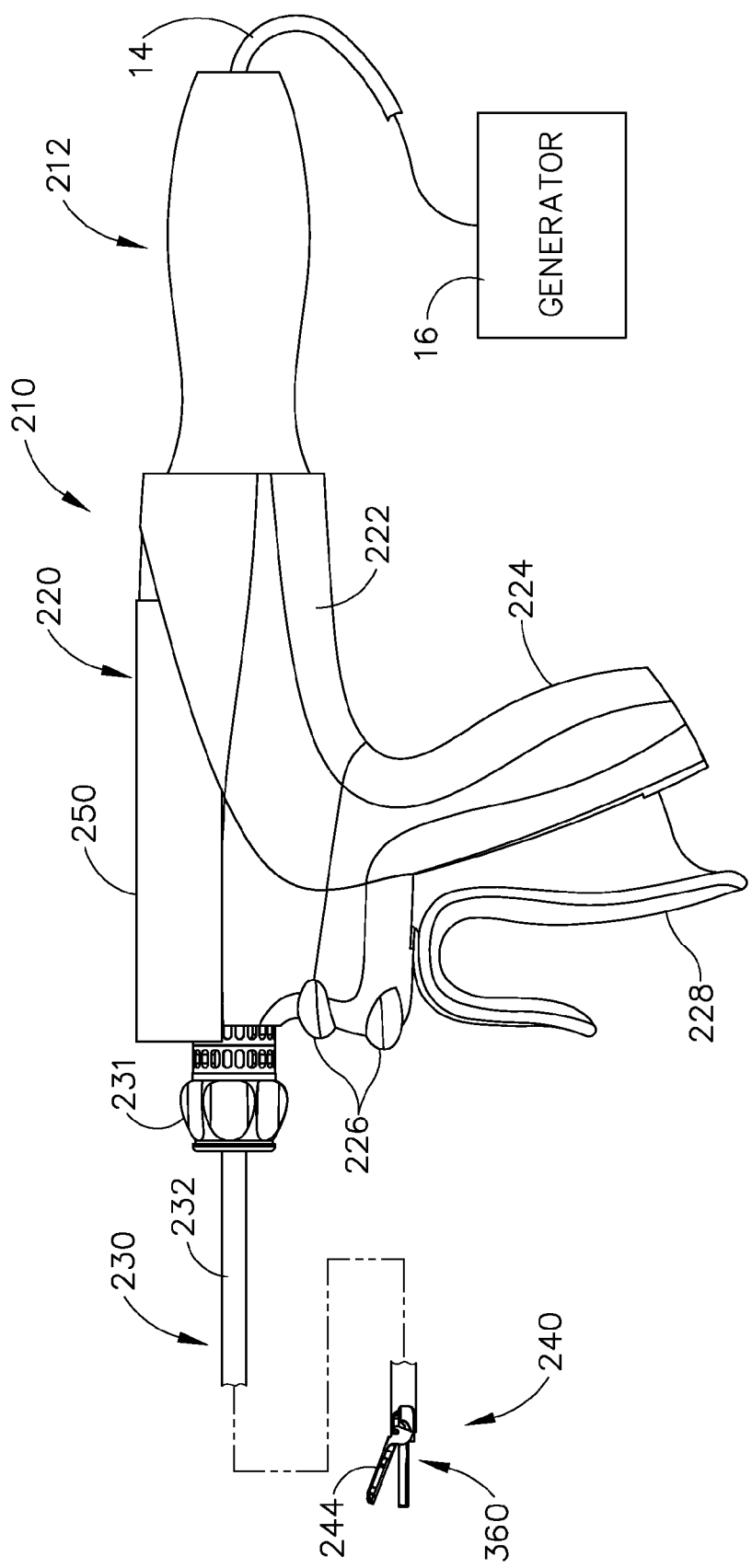
FIG. 22 depicts a side elevational view of another exemplary ultrasonic surgical instrument with a loading assembly.

FIG. 22 shows an exemplary ultrasonic surgical instrument (210) that is similar to instrument (10) in that instrument (210) comprises a handle assembly (220), a shaft assembly (230), and a transducer assembly (212). Instrument (210) further comprises a loading assembly (250). End effector (240) is similar to end effector (40, 140) In that end effector (240) comprises an ultrasonic blade (360) and a clamp arm (244). Handle assembly (220) is similar to handle assembly (20, 120) in that handle assembly (220) comprises a body (222) including a pistol grip (224), a pair of buttons (226), and a trigger (228) that is pivotable toward and away from pistol grip (224). Trigger (228) is operable to pivot clamp arm (244) of end effector (240) toward and away from blade (360) to selectively clamp tissue between clamp arm (244) and blade (360). Blade (360) is operable to vibrate at ultrasonic frequencies in order to effectively cut through and seal tissue, particularly when the tissue is being clamped between clamp arm (244) and blade (360).

Figure 24:
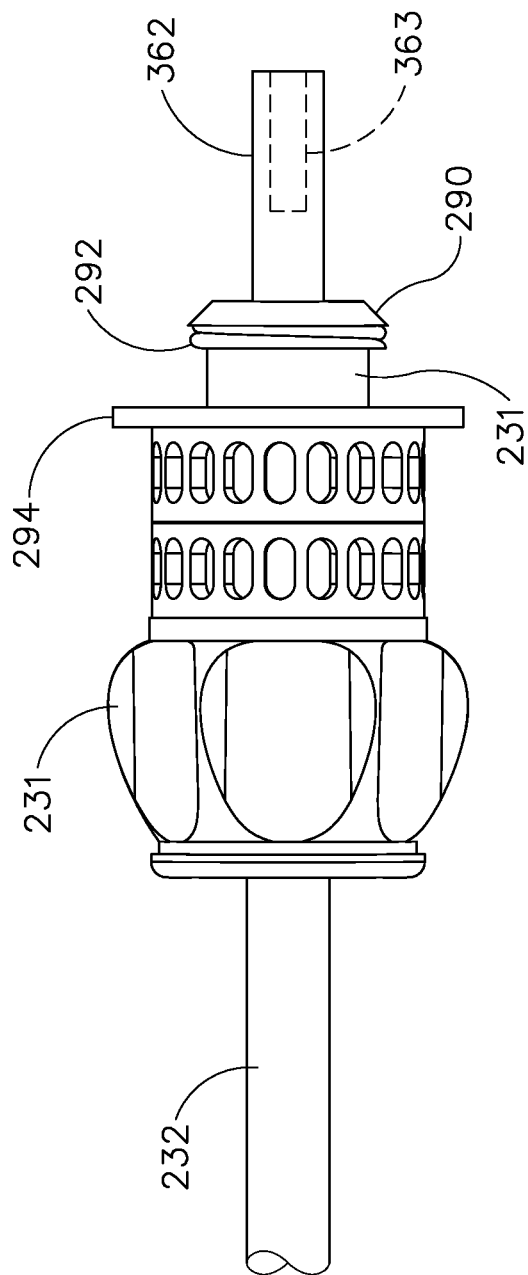
FIG. 24 depicts a side elevational view of a proximal end of a shaft assembly of the instrument of FIG. 22.

End effector (240) is coupled to a distal end of shaft assembly (230). Shaft assembly (230) is similar to shaft assembly (30, 130), in that shaft assembly (230) comprises an outer sheath (232), an inner tube (234), and a waveguide (362). The proximal end of waveguide (362) is selectively removable from transducer assembly (212). As shown in FIG. 24, the proximal end of waveguide (362) extends proximally from the proximal end of inner tube (234). The proximal end of waveguide (362) includes a threaded recess (363) that may be coupled with transducer assembly (212), which is similar to transducer assembly (112) described above. Shaft assembly (230) further comprises a bevel gear (290) positioned on waveguide (362). Bevel gear (290) is fixedly secured to waveguide (262) such that bevel gear (290) and waveguide (262) rotate unitarily. In some versions, bevel gear (290) is secured to waveguide (262) at a location corresponding to a node associated with ultrasonic vibrations communicated through waveguide (262). A resilient member (292) is distal to bevel gear (290).

A plate (294) is removably coupled with rotation knob (231) to prevent shaft assembly (230) from rotating relative to handle assembly (220) while shaft assembly (230) is being coupled with transducer assembly (212). In particular, plate (294) is mounted within handle assembly (220) with a resilient distal bias, such that plate (294) is resiliently biased to engage a proximal face of rotation knob (231). In some versions, this distal bias against plate (294) is provided by resilient member (292) described below. When plate (294) engages the proximal face of rotation knob (231), plate (294) provides friction against the proximal face of rotation knob (231), such that plate (294) acts as a brake to prevent rotation of shaft assembly (230) relative to handle assembly (220). However, as will be described in greater detail below, plate (294) may be translated proximally within handle assembly (220) to thereby disengage the proximal face of rotation knob (231). When plate (294) is disengaged from the proximal face of rotation knob (231), shaft assembly (230) is free to rotate relative to handle assembly (220).

Figure 23:
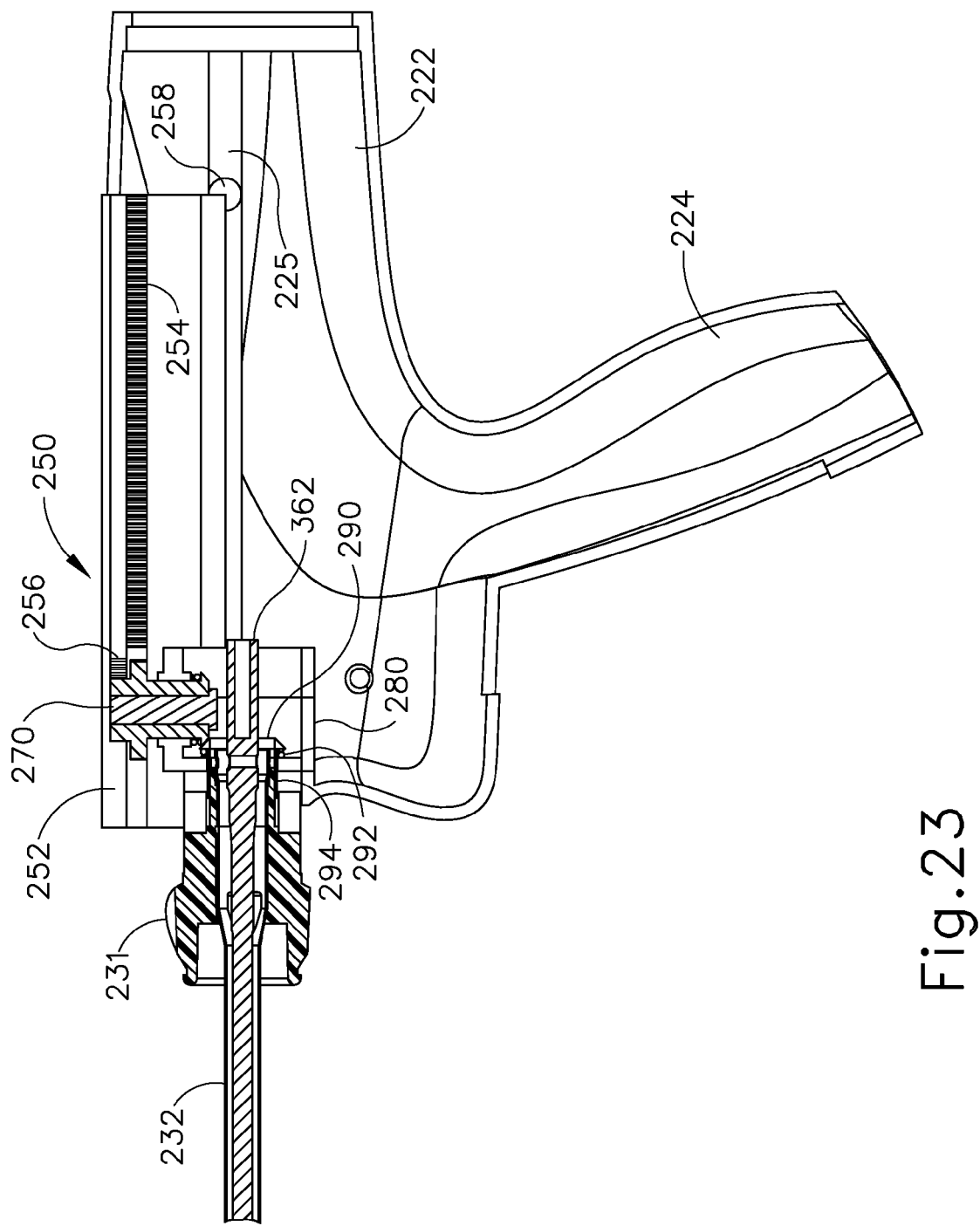
FIG. 23 depicts a cross sectional view of a handpiece assembly of the instrument of FIG. 22 showing the loading assembly.
Figure 25:
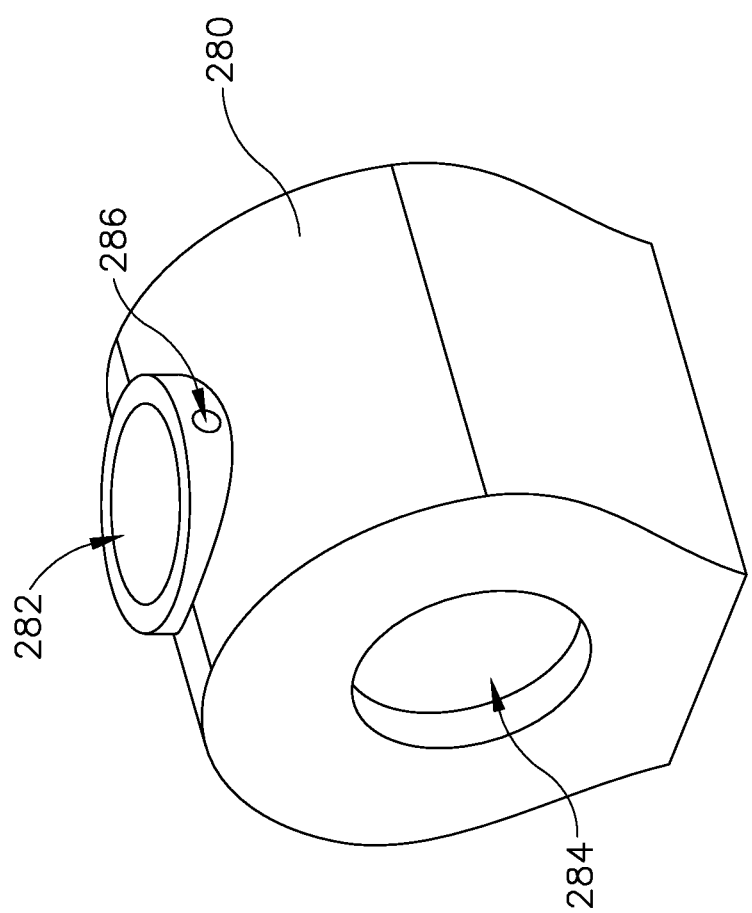
FIG. 25 depicts a perspective view of a housing of the loading assembly of FIG. 22.
Figure 26:
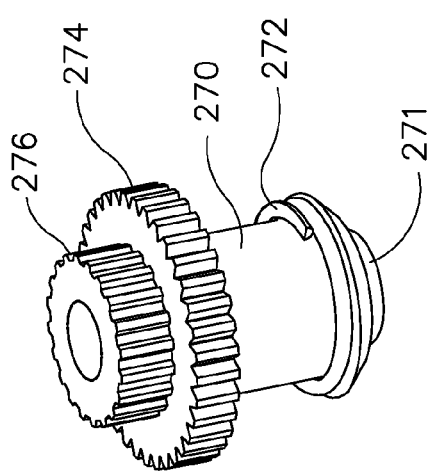
FIG. 26 depicts a perspective view of a coupling gear of the loading assembly of FIG. 22.
Figure 28:
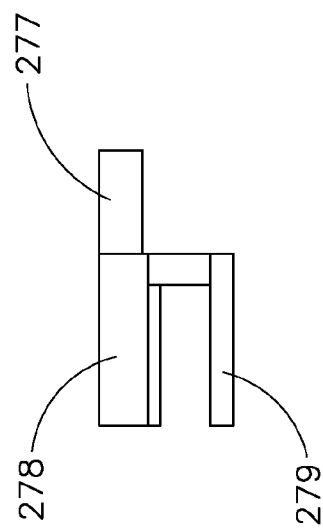
FIG. 28 depicts a front elevational view of the ratchet arm of FIG. 27.
Figure 27:
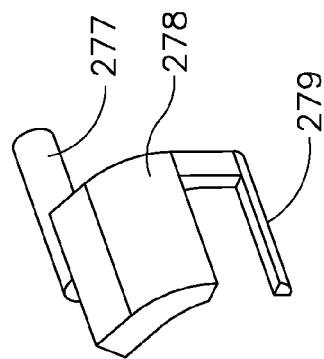
FIG. 27 depicts a perspective view of a ratchet arm of the loading assembly of FIG. 22.
Figure 29:
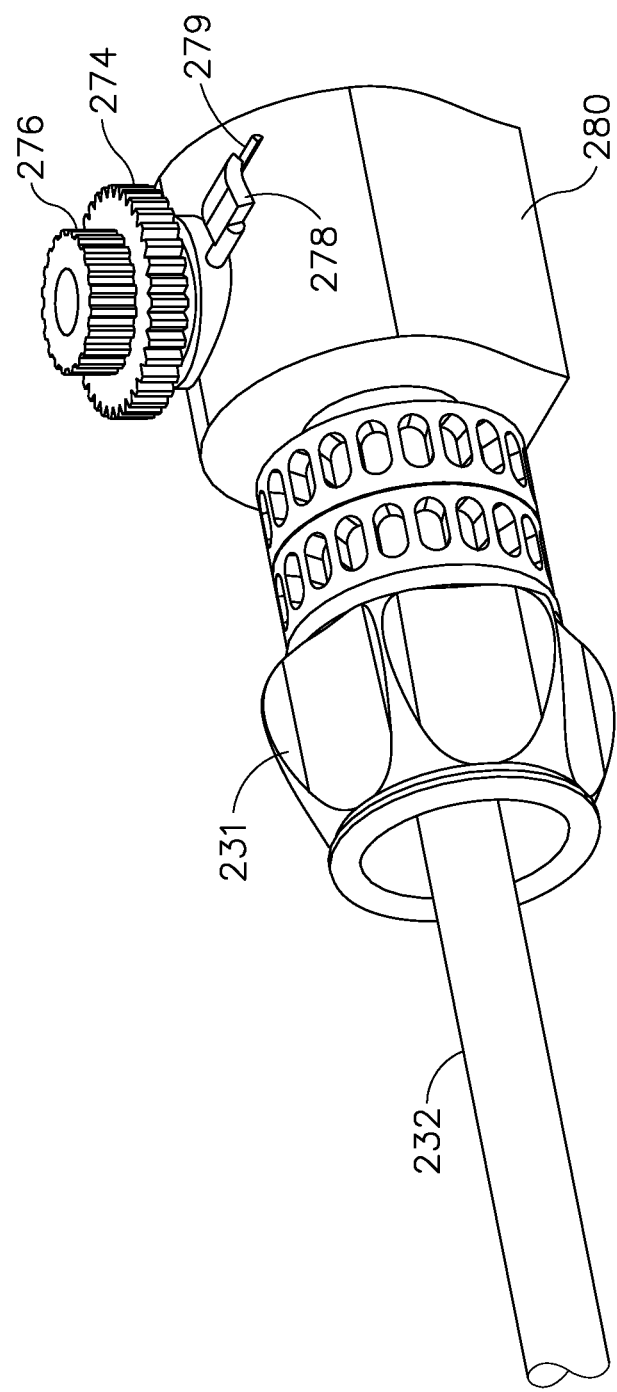
FIG. 29 depicts a perspective view of the shaft assembly of FIG. 24 coupled with the housing of FIG. 25 and the coupling gear of FIG. 26.

As shown in FIG. 23, shaft assembly (230) is positioned within loading assembly (250) to couple shaft assembly (230) with transducer assembly (212). Loading assembly (250) is coupled with body (222) of handle assembly (220) and comprises a housing (280), a coupling gear (270), and an actuator (252). Housing (280) is fixedly secured within body (222). FIG. 25 shows housing (280) in more detail. Housing (280) comprises a first opening (284) and a second opening (282), which is perpendicular to first opening (284). First opening (284) is configured to receive shaft assembly (230). As shown in FIGS. 23 and 29, shaft assembly (230) is positioned within first opening (284) of housing (280) such that bevel gear (290) and resilient member (292) are located within housing (280), while plate (294) is located distal to housing (280). Second opening (282) of housing (280) is configured to receive coupling gear (270), as will be discussed in more detail. As shown in FIGS. 26-28, coupling gear (270) comprises a first spur gear (276) and a second spur gear (274) that has a larger diameter than first spur gear (276). First and second spur gears (276, 274) are coaxially aligned with each other. An opposing end of coupling gear (270) comprises a bevel gear (271) and a resilient member (272).

Referring back to FIGS. 23 and 29, coupling gear (270) is positioned within second opening (282) of housing (280) such that first and second spur gears (274, 276) are located outside of housing (280), while resilient member (272) and bevel gear (271) are located within housing (280). Of course, other suitable configurations for housing (280) will be apparent to one with ordinary skill in the art in view of the teachings herein. With coupling gear (280) and shaft assembly (230) positioned within housing (280) of loading assembly (280), bevel gear (271) of coupling gear (270) meshes with bevel gear (290) of shaft assembly (230).

Resilient members (272, 292) press against housing (280) to bias bevel gears (271, 290) towards each other to prevent slipping between bevel gears (271, 290). In this position, first spur gear (276), second spur gear (274), and ratchet arm (278) of coupling gear (270) are configured to engage actuator (252).

Loading assembly (250) of the present example further comprises a ratchet arm (278). As best seen in FIGS. 27-28, ratchet arm (278) includes an integral pivot pin (277) and an integral pawl (279). Pivot pin (277) is pivotably disposed in a third opening (286) of housing (280). Ratchet arm (278) is configured to ratchet pawl (279) against a rack (257) during operation of loading assembly (250), as will be described in greater detail below.

Figure 30:
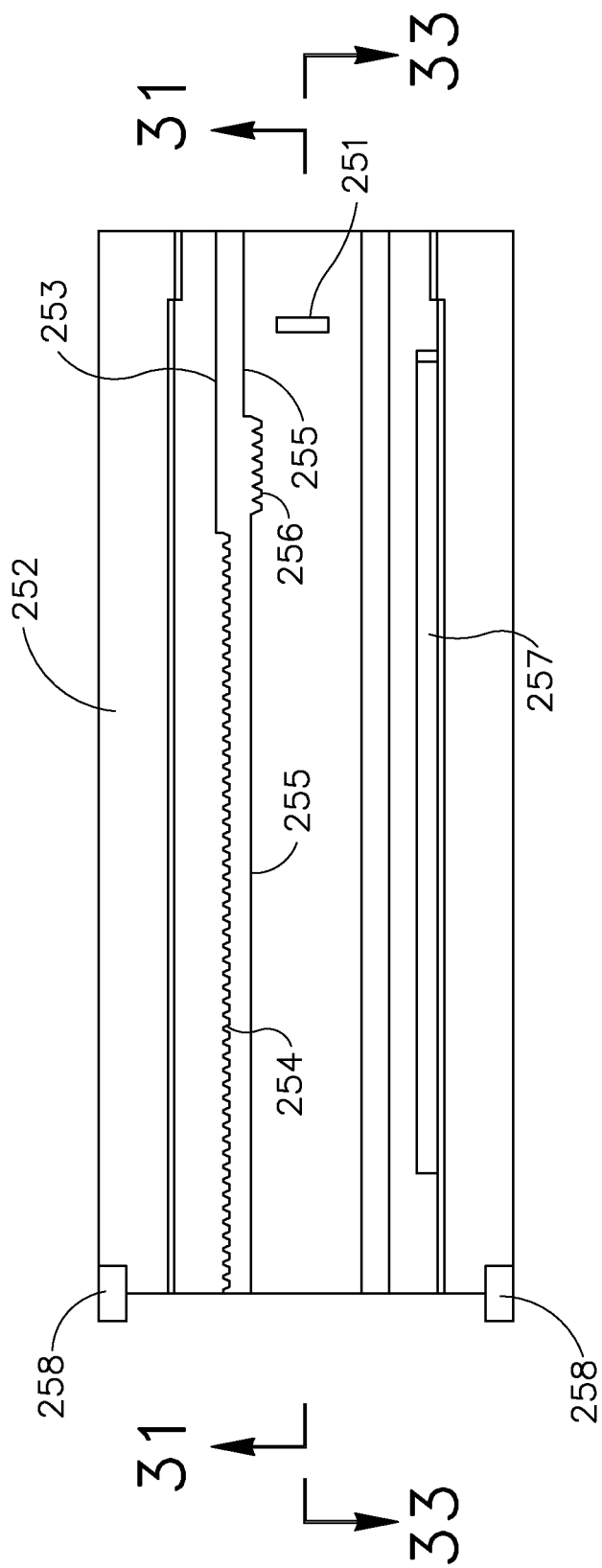
FIG. 30 depicts a bottom plan view of an actuator of the loading assembly of FIG. 22.

FIGS. 30-33 show actuator (252) of loading assembly (250) in greater detail. FIG. 30 depicts a bottom view of actuator (252) that shows a first rack (256), a second rack (254), a third rack (257), and a distal tab (251) of actuator (252). As best seen in FIGS. 31-32, the interior portion of a first side of actuator (252) comprises a first rack (256) and a second rack (254). First rack (256) is distal to second rack (254) and is laterally offset from second rack (254) such that first rack (256) extends more inwardly within actuator (252) than second rack (254). First rack (256) is also vertically offset from second rack (254). Accordingly, first rack (256) is configured to engage first spur gear (276). The teeth of first rack (256) are positioned distal to a smooth portion (255). Second rack (254) is positioned proximal to a smooth portion (253) and is configured to engage second spur gear (274). Actuator (252) further comprises a protrusion (258) on each side of actuator (252) that is configured to translate within channels (225) extending longitudinally along the sidewalls of body (222). Accordingly, actuator (252) is longitudinally translatable relative to handle assembly (220). Actuator (252) may be pulled proximally such that racks (254, 256) engage spur gears (274, 276) in a sequence to thereby rotate coupling gear (270). As described above, coupling gear (270) then rotates bevel gear (290) on waveguide (262) to rotate waveguide (262) relative to transducer assembly (212). This threads recess (363) of waveguide (362) onto threaded stud (67) of horn (66).

Actuator (252) further comprises a tab (251) extending inwardly on a distal portion of actuator (252). Tab (251) is configured to engage plate (294) of shaft assembly (230) as actuator (252) is translated proximally. In particular, tab (251) is operable to drive plate (294) proximally within handle assembly (220), to thereby decouple plate (294) from the proximal face of rotation knob (231). This allows rotation knob (231) and shaft assembly (230) to rotate freely relative to handle assembly (220) after shaft assembly (230) is coupled with transducer assembly (212).

Figure 33:
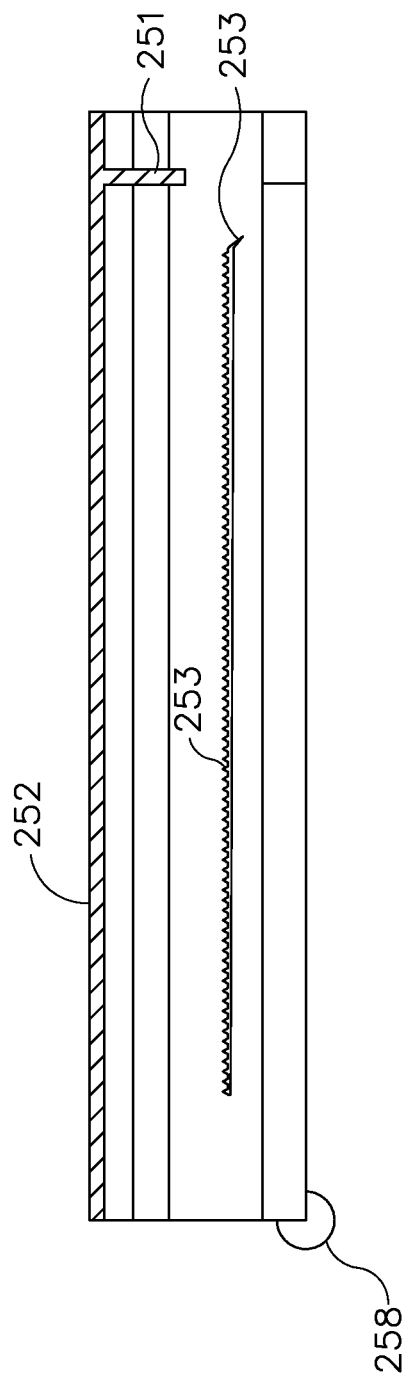
FIG. 33 depicts a side cross-sectional view of the actuator of FIG. 30, taken along line 33-33 of FIG. 30, showing a third rack.

As shown in FIG. 33, actuator (252) further comprises a third rack (257) extending along the opposing interior side of actuator (252). Third rack (257) is configured to engage ratchet arm (278). In particular, pawl (279) of ratchet arm (278) is positioned to engage the teeth of third rack (257). In some versions, a resilient feature (e.g., torsion spring, etc.) is used to resiliently bias pawl (279) into engagement with the teeth of third rack (257). When actuator (252) is translated proximally, pawl (279) translates along third rack (257) to provide a tactile and/or audible feedback to the user. In addition, pawl (279) provides a one-way ratcheting effect that prevents actuator (252) from being translated distally while actuator (252) is being transitioned from a distal position to a proximal position. After actuator (252) is translated proximally, pawl (279) of ratchet arm (278) disengages third rack (257). In particular, ratchet arm (278) pivots such that pawl (279) falls below third rack (257) at the end of the stroke. After use of instrument (210), actuator (252) may be translated distally to decouple shaft assembly (230) with transducer assembly (212). When actuator (252) is translated distally, third rack (257) translates distally above pawl (279) of ratchet arm (278) such that third rack (257) does not engage pawl (279) of ratchet arm (278). The distal end of third rack (257) comprises a ramp (259) that cams against pawl (279) to again place pawl (279) above third rack (257) such that pawl (279) engages the teeth of third rack (257) when actuator (252) is again translated proximally. Of course, other configurations for third rack (257) will be apparent to one with ordinary skill in the art in view of the teachings herein.

Figure 34A:
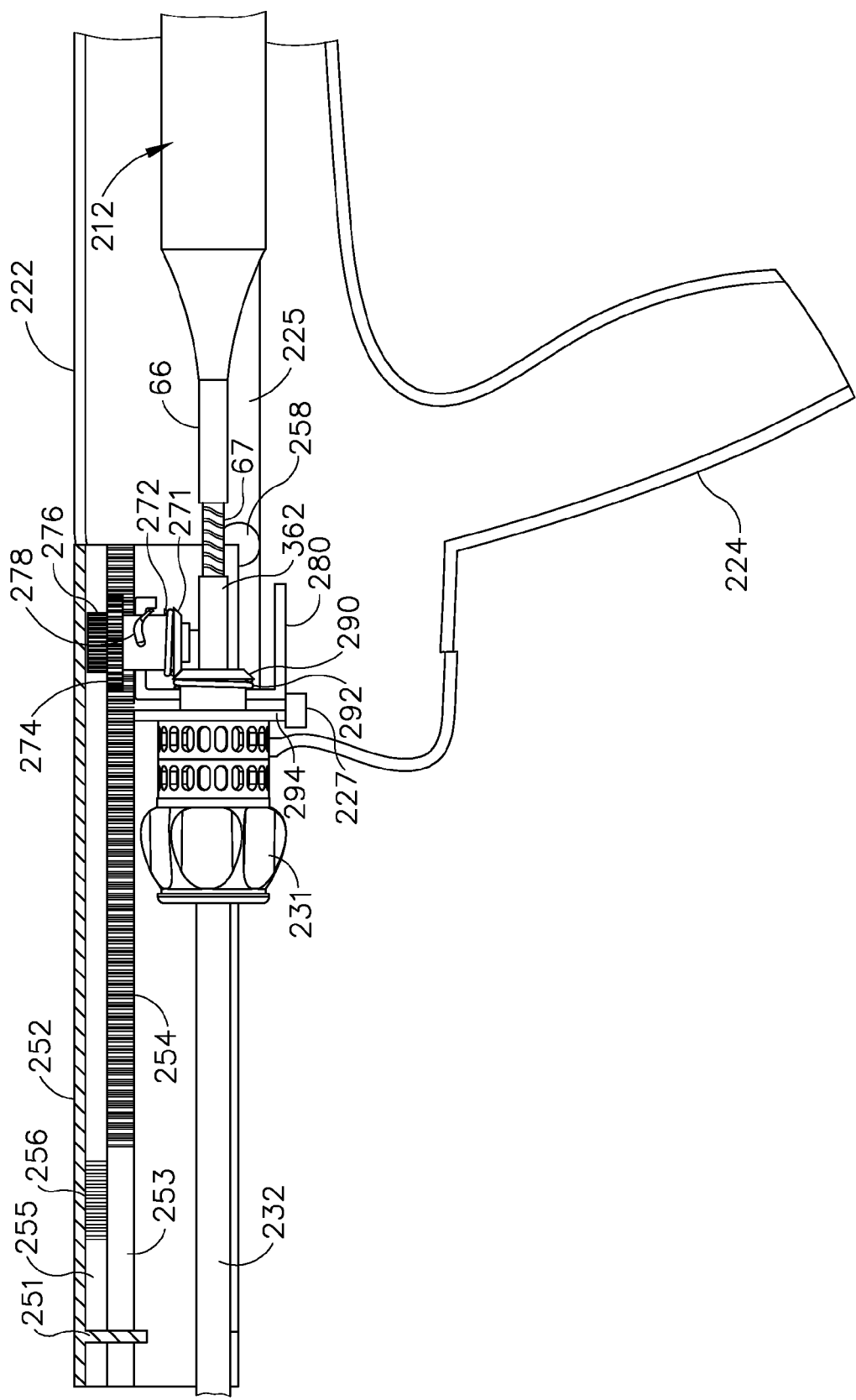
FIG. 34A depicts a cross sectional view of the instrument of FIG. 22 with the transducer assembly detached from the shaft assembly.
Figure 34B:
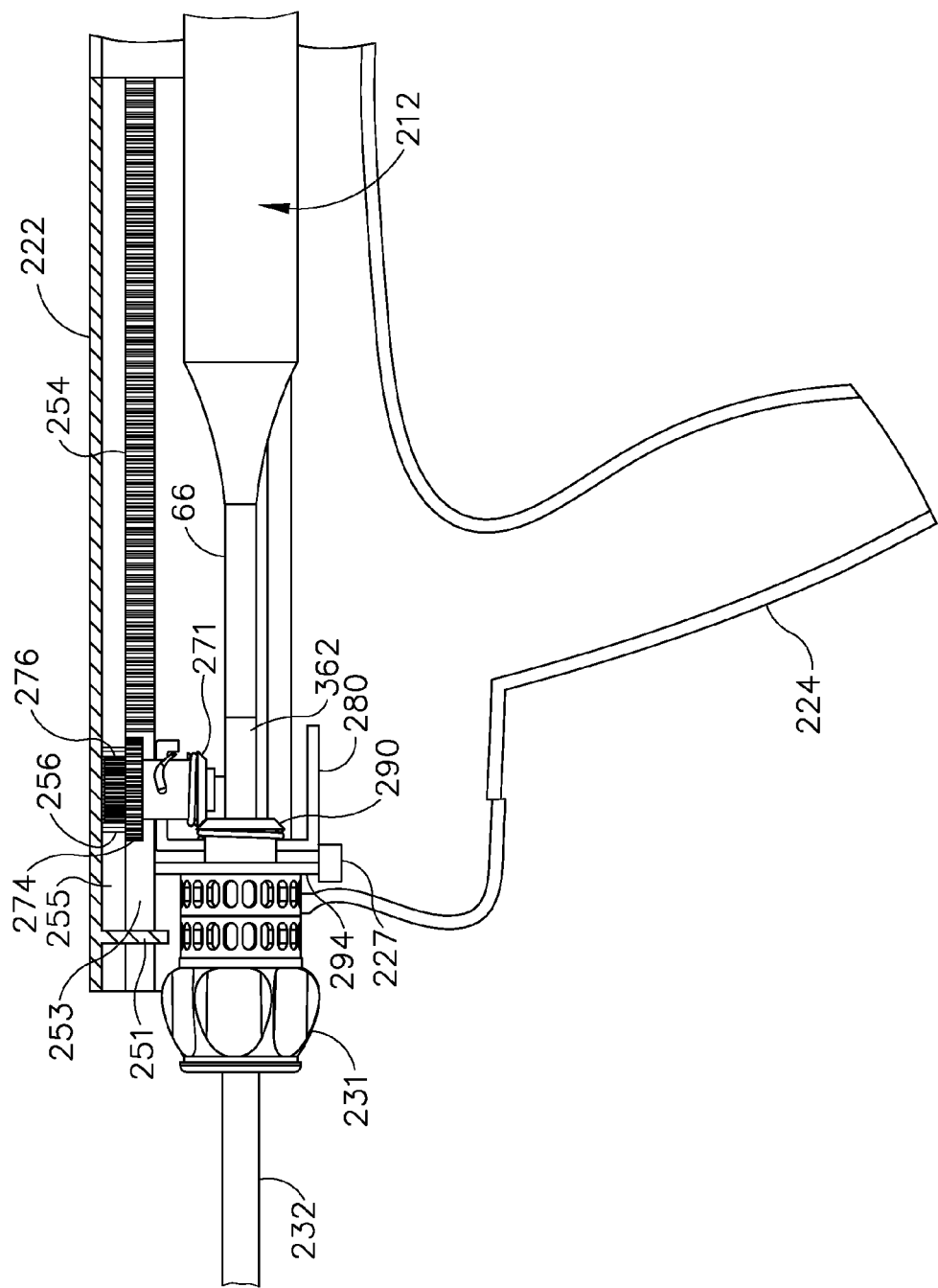
FIG. 34B depicts a cross sectional view of the instrument of FIG. 22 with the shaft assembly partially coupled with the transducer assembly.
Figure 34C:
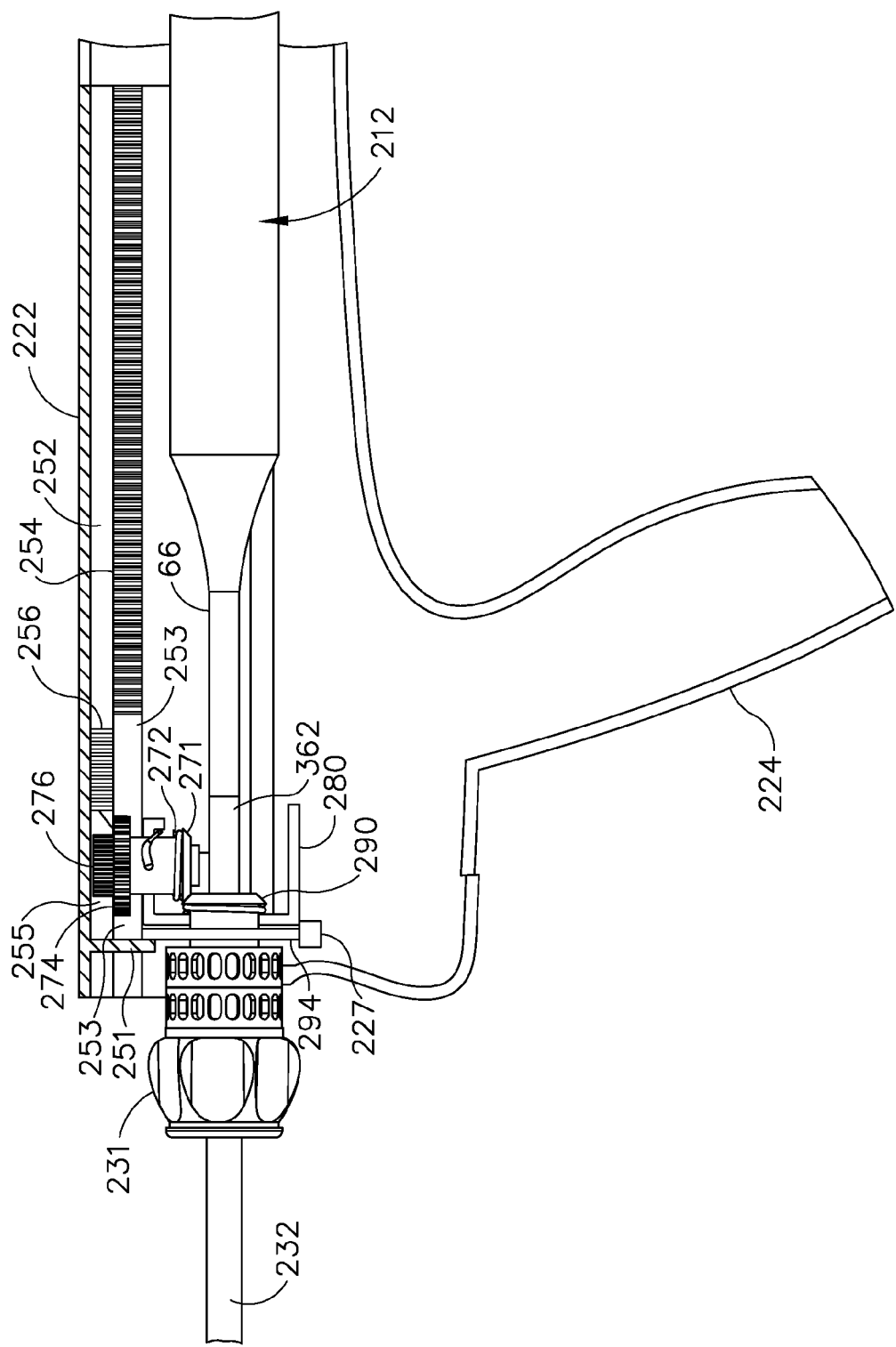
FIG. 34C depicts a cross sectional view of the instrument of FIG. 22 with the shaft assembly fully coupled with the transducer assembly.

FIGS. 34A-34C show an exemplary operation of loading assembly (250). As shown in FIG. 34A, the proximal end of shaft assembly (230) is positioned within first opening (284) of housing (280). In particular, first opening (284) is sized to allow bevel gear (290) of shaft assembly (230) to pass freely into housing (280). Bevel gear (290) of shaft assembly (230) engages bevel gear (271). Resilient member (292) and bevel gear (290) of shaft assembly (230) are thus positioned within housing (280), while plate (294) of shaft assembly (230) is positioned distal to housing (280). Plate (294) is engaged with a tab (227) on body (222). Tab (227) engages urges plate (294) against the proximal face of rotation knob (231) and prevents plate (294) from rotating. Plate (294) thus prevents rotation of shaft assembly (230) relative to handle assembly (220).

First spur gear (276) is aligned with first rack (256) of actuator (252) and second spur gear (274) is aligned with second rack (254) of actuator (252). Actuator (252) is in a distal position relative to body (222) such that second spur gear (274) is engaged with second rack (254). First spur gear (276) is located within a smooth portion (255) of first rack (256). Threaded stud (67) of transducer assembly (212) is positioned adjacent to the proximal end of waveguide (362) such that threaded stud (67) is coaxially aligned with threaded recess (363).

Actuator (252) is then translated proximally relative body (222) of handle assembly (220). Protrusions (258) of actuator (252) slide within channels (225) of body (222) as actuator (252) is translated to maintain alignment of actuator (252) with body (222). When actuator (252) is translated proximally, second rack (254) engages second spur gear (274) to rotate second spur gear (274) at a relatively high speed, and at a relatively low torque. Second spur gear (274) thereby rotates bevel gear (271) of coupling gear (270), which rotates the other bevel gear (290) on shaft assembly (230). Rotation of bevel gear (290) rotates waveguide (362), to thereby thread recess (363) onto threaded stud (67) of transducer assembly (212). As noted above, plate (294) engages tab (227) of body (222) and rotation knob (231) to prevent rotation of rotation shaft assembly (230) (including waveguide (362), etc.) during proximal translation of actuator (252).

As shown in FIG. 34B, actuator (252) continues to translate proximally such that the teeth of first rack (256) eventually engage first spur gear (276) to rotate first spur gear (276) at a lower speed and higher torque than second spur gear (274). Second spur gear (274) disengages the teeth of second rack (254) and enters smooth portion (253) of second rack (254) when first rack (256) engages first spur gear (276). The rotation of first spur gear (276) further rotates bevel gear (271) of coupling gear (270), which further rotates bevel gear (290) on shaft assembly (230). Rotation of bevel gear (290) further rotates waveguide (362)

further, to thereby further thread recess (363) onto threaded stud (67) of transducer assembly (212). As actuator (252) is pulled proximally, ratchet arm (278) of coupling gear (270) engages third rack (257) to provide tactile and/or audible feedback to the user; and to prevent actuator (252) from slipping distally in relation to handle assembly (220).

As actuator (252) is translated further proximally, first spur gear (276) disengages the teeth of first rack (256) and enters smooth portion (255) of first rack (256), as shown in FIG. 34C. Accordingly, waveguide (362) is coupled with transducer assembly (212) at am appropriate amount of torque. By the time actuator (252) reaches the proximal position shown in FIG. 34C, tab (251) of actuator (252) has engaged plate (294) of shaft assembly (230) to translate plate (294) proximally. Plate (294) is thus decoupled from the proximal face of rotation knob (231), such that shaft assembly (230) is free to rotate relative to body (222) to rotate end effector (240). Ratchet arm (278) of coupling gear (270) is further disengaged from third rack (257) of actuator (252) at this stage. With shaft assembly (230) fully coupled with transducer assembly (212), trigger (228) may be pivoted relative to pistol grip (224) to thereby pivot clamp arm (244) of end effector (240) toward and away from blade (360) to selectively clamp tissue between clamp arm (244) and blade (360). Buttons (226) may then be pressed to activate transducer assembly (212) and thereby activate blade (360) to vibrate at ultrasonic frequencies in order to effectively cut through and seal tissue.

After use of instrument (210), shaft assembly (230) may be detached from transducer assembly (212). Actuator (252) of loading assembly (250) may be translated distally relative to body (222) such that first rack (256) rotates first spur gear (276), bevel gear (271), and bevel gear (290) in the opposing direction to unthread transducer assembly (212) from shaft assembly (230). Third rack (257) of actuator (252) translates distally without engaging ratchet arm (278) of coupling gear (270). As actuator (252) continues to translate distally, first rack (256) disengages first spur gear (276) and second rack (254) engages second spur gear (274) to continue rotating bevel gears (271, 290). Plate (294) may translate to a distal position to prevent shaft assembly (230) from rotating relative to handle assembly (220). In addition or in the alternative, the operator may grasp knob (231) to prevent shaft assembly (230) from rotating relative to handle assembly (220). Regardless of how shaft assembly (230) is rotatable secured, waveguide (362) is rotated to decouple waveguide (362) from horn (66) to release shaft assembly (230) from transducer assembly (212). Shaft assembly (230) and/or transducer assembly (212) may then be removed from instrument (210). Other suitable configurations and operabilities for a loading assembly (150, 250) will be apparent to those of ordinary skill in the art in view of the teachings herein.

III. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention.

Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a shaft assembly extending distally from the body;
   (c) an end effector coupled with a distal end of the shaft assembly, wherein the end effector is operable to manipulate tissue;
   (d) a transducer assembly, wherein the transducer assembly is operable to convert electrical power into ultrasonic vibrations, wherein a distal end of the transducer assembly is configured to removably couple with a proximal end of the shaft assembly; and
   (e) a loading assembly, wherein the loading assembly comprises an actuator configured to selectively move from a first position to a second position to thereby couple the distal end of the transducer assembly with the proximal end of the shaft assembly, wherein the loading assembly is configured to rotatably drive the transducer assembly successively through a first stage of rotation and a second stage of rotation when moving the actuator from the first position to the second position, wherein the loading assembly during the first stage of rotation is configured to rotatably drive the transducer assembly with a first rotational speed and a first rotational torque, wherein the loading assembly during the second stage of rotation is configured to rotatably drive the transducer assembly with a second rotational speed and a second rotational torque, wherein the second rotational speed is less than the first rotational speed, and wherein the second rotational torque is greater than the first rotational torque for coupling the distal end of the transducer assembly with the proximal end of the shaft assembly.

2. The instrument of claim 1, wherein the loading assembly comprises a first spur gear and a second spur gear, wherein the second spur gear has a larger diameter than the first spur gear.

3. The instrument of claim 2, wherein the loading assembly comprises a first rack and a second rack, wherein the first rack is configured to engage the first spur gear and the second rack is configured to engage the second spur gear.

4. The instrument of claim 3, wherein first rack is translatable to rotate the first spur gear, wherein the second rack is translatable to rotate the second spur gear, wherein the first spur gear is configured to rotate at a higher speed than the second spur gear, wherein the second spur gear is configured to rotate at a higher torque than the first spur gear.

5. The instrument of claim 3, wherein the first rack extends along an arcuate path, wherein the second rack extends along an arcuate path.

6. The instrument of claim 2, wherein the first rack is configured to engage the first spur gear during the first stage of rotation, wherein the second rack is configured to engage the second spur gear during the second stage of rotation.

7. The instrument of claim 6, wherein the first rack is configured to disengage the first spur gear during the second stage of rotation.

8. The instrument of claim 1, further comprising a bevel gear secured to a portion of the shaft assembly, wherein the bevel gear is configured to engage the loading assembly.

9. The instrument of claim 1, wherein the actuator is configured to translate relative to the body.

10. The instrument of claim 9, wherein the actuator is operable to translate through a first range of longitudinal motion to provide the first stage of rotation of the transducer assembly, wherein the actuator of the loading assembly is operable to translate through a second range of longitudinal motion to provide the second stage of rotation of the transducer assembly.

11. The instrument of claim 1, wherein the shaft assembly defines a longitudinal axis, wherein the actuator is rotatable about an axis that is perpendicular to the longitudinal axis.

12. The instrument of claim 1, wherein the loading assembly comprises a rotation locking member configured to selectively prevent rotation of the shaft assembly relative to the body.

13. The instrument of claim 12, wherein the loading assembly comprises a feature configured to selectively disengage the rotation locking member, to thereby permit rotation of the shaft assembly relative to the body.

14. The instrument of claim 1, wherein the actuator comprises a lever that is pivotable relative to the body to couple the distal end of the transducer assembly with the proximal end of the shaft assembly.

15. The instrument of claim 1, wherein the actuator is translatable relative to the body to couple the distal end of the transducer assembly with the proximal end of the shaft assembly.

16. The instrument of claim 1, wherein the loading assembly comprises a ratcheting feature configured to provide one or both of user feedback or one-way movement restriction during actuation of the loading assembly.

17. The instrument of claim 1, wherein at least a portion of the loading assembly is housed within the body.

18. The instrument of claim 1, wherein the end effector comprises an ultrasonic blade and a pivoting clamp arm.

19. A surgical instrument comprising:
   (a) a shaft assembly;
   (b) a transducer assembly, wherein a distal end of the transducer assembly is configured to removably couple with a proximal end of the shaft assembly; and
   (c) a loading assembly, wherein the loading assembly comprises an actuator that is configured to move through a first range of motion and a second range of motion, wherein the loading assembly is configured to couple the distal end of the transducer assembly with the proximal end of the shaft assembly at a first speed and a first torque during the first range of motion, wherein the loading assembly is configured to couple the distal end of the transducer assembly with the proximal end of the shaft assembly at a second speed and a second torque during the second range of motion, wherein the second speed is less than the first speed, and wherein the second torque is greater than the first torque.

20. A method of operating a surgical instrument, wherein the instrument comprises a shaft assembly, a transducer assembly configured to removably couple with a proximal end of the shaft assembly, and a loading assembly, the method comprising the step of:
   (a) positioning a proximal end of the shaft assembly adjacent to a distal end of the transducer assembly;

(b) actuating the loading assembly to couple the shaft assembly with the transducer assembly at a first speed and a first torque; and
(c) actuating the loading assembly to couple the shaft assembly with the transducer assembly at a second speed and a second torque, wherein the second speed is slower than the first speed, and wherein the second torque is greater than the first torque.

* * * * *